United States Patent
Gray et al.

(10) Patent No.: US 10,537,650 B2
(45) Date of Patent: Jan. 21, 2020

(54) MOLECULAR PROBES FOR MULTIMODALITY IMAGING AND TRACKING OF STEM CELLS

(71) Applicant: University of Massachusetts, Boston, MA (US)

(72) Inventors: Brian D. Gray, Malvern, PA (US); Mary Rusckowski, Southborough, MA (US); Koon Y. Pak, Malvern, PA (US)

(73) Assignee: University of Massachusetts, Boston, MA (US)

( * ) Notice: Subject to any disclaimer, the term of this patent is extended or adjusted under 35 U.S.C. 154(b) by 0 days.

(21) Appl. No.: 15/350,389

(22) Filed: Nov. 14, 2016

(65) Prior Publication Data

US 2017/0239377 A1 Aug. 24, 2017

Related U.S. Application Data

(63) Continuation of application No. 14/400,757, filed as application No. PCT/US2013/042786 on May 27, 2013, now Pat. No. 9,492,571.

(60) Provisional application No. 61/654,794, filed on Jun. 1, 2012.

(51) Int. Cl.
| | | |
|---|---|---|
| *A61K 51/04* | (2006.01) |
| *A61K 49/00* | (2006.01) |
| *G01N 33/50* | (2006.01) |
| *C07D 209/14* | (2006.01) |
| *C07B 59/00* | (2006.01) |
| *C07D 209/20* | (2006.01) |
| *C07D 403/14* | (2006.01) |
| *G01N 33/58* | (2006.01) |
| *G01N 33/52* | (2006.01) |
| *G01N 33/569* | (2006.01) |

(52) U.S. Cl.
CPC ...... *A61K 51/0485* (2013.01); *A61K 49/0032* (2013.01); *A61K 51/0446* (2013.01); *A61K 51/0478* (2013.01); *A61K 51/0482* (2013.01); *C07B 59/002* (2013.01); *C07D 209/14* (2013.01); *C07D 209/20* (2013.01); *C07D 403/14* (2013.01); *G01N 33/5005* (2013.01); *G01N 33/52* (2013.01); *G01N 33/56966* (2013.01); *G01N 33/582* (2013.01)

(58) Field of Classification Search
CPC ...... A61K 49/00; A61K 31/555; A61K 51/04; A61B 5/145
See application file for complete search history.

(56) References Cited

U.S. PATENT DOCUMENTS

2014/0248213 A1\* 9/2014 Chung ............... C09B 23/0016
424/1.85

\* cited by examiner

*Primary Examiner* — Michael G. Hartley
*Assistant Examiner* — Jagadishwar R Samala
(74) *Attorney, Agent, or Firm* — Milstein Zhang & Wu LLC

(57) ABSTRACT

The invention relates to novel multi-modality probes for imaging, tracking and analyzing stem cells and related biological samples, and methods of preparation and use thereof. The molecular probes of the invention are constructed, for example, by utilizing (a) the high selectivity of long hydrocarbon chains for binding to plasma membranes of cells, (b) a near-infrared (NIR) dye for optical imaging, and (c) a radionuclide for PET or SPECT imaging. The in vitro and in vivo data of the optical and radiolabeled probes demonstrated their utility for detecting the presence of stem cells with multiple imaging modalities.

19 Claims, 18 Drawing Sheets

(a)

(b)

MOLECULAR PROBES FOR MULTIMODALITY IMAGING AND TRACKING OF STEM CELLS

PRIORITY CLAIMS AND RELATED PATENT APPLICATIONS

Figure 1:
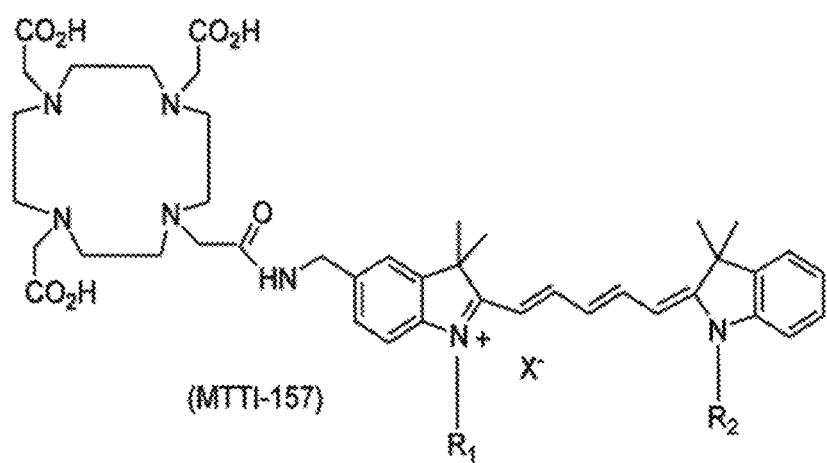

This application claims the benefit of U.S. patent application Ser. No. 14/400,757, filed Nov. 12, 2014, which is the U.S. national phase of PCT/US2013/042786, filed on May 27, 2013, which claims the benefit of priority from U.S. Provisional Application Ser. No. 61/654,794, filed on Jun. 1, 2012, the entire content of which is incorporated herein by reference in its entirety for all purposes.

STATEMENT REGARDING FEDERALLY FUNDED RESEARCH

This invention was made with government support under Grant No. GM093417 awarded by the National Institutes of Health. The Government has certain rights in the invention.

TECHNICAL FIELDS OF THE INVENTION

The invention generally relates to imaging probes. More particularly, the invention relates to novel multi-modality probes for imaging, tracking and analyzing stem cells and related biological samples, and methods of preparation and use thereof.

BACKGROUND OF THE INVENTION

Stem cell therapies have the potential to dramatically change the treatment of a number of diseases such as Parkinson's, Alzheimer's, spinal cord injury, diabetes, ischemia stroke and heart disease. Although tremendous achievements and rapid developments have been made in the past decade for cell-based therapies of a number of disease states, the potential that stem cells offer remains to be better understood. One of the concerns with stem cell therapies is the risk that transplanted stem cells could form tumors and become cancerous if cell division continues uncontrollably. Critical insights can be achieved by observing their fate in vivo overtime using noninvasive imaging techniques.

An emerging technology that allows for visualization of interactions between molecular probes and biological targets is molecular imaging, which can be divided into two general categories: (1) the direct labeling method, and (2) the reporter gene approach. The former involves using an imaging-detectable probe that can be loaded into cells and would remain intracellular during tracking. This method does not involve extensive manipulation of cells and therefore is preferred for clinical implementation. It has two inherent limitations: labels may be diluted upon cell division, making the cells eventually invisible; and labels may efflux from cells or may degrade over time. Examples of contrast agents are FDG for PET, $^{111}$In-oxine for SPECT and iron nanoparticles (SPIOs) for MRI, which have significant limitations. (Zhang, et al. 2008 *Current Pharma. Design* 14 (36): 3835-3853; Zhou, et al. 2006 *JACC* 48 (10): 2094-2106.)

The reporter gene approach is used mostly for preclinical studies. (Narsinh, et al. 2009 Molecular Imaging of Human Embryonic Stem Cells. Ch 2 p 13-32; in *Methods in Molecular Biology, Viral Applications of Green Fluorescent Protein*, Vol. 515. Barry W Hicks (Ed) Humana Press.) This approach involves inserting a reporter gene(s) into the stem cell that can then be tracked upon administration of a reporter probe. Reporter genes are useful for assessing the longer-term survival of the implanted cells because the reporter will be expressed as long as the cells are alive. Major disadvantages of the reporter gene approach include: (i) stable transfection (lentiviral or retroviral) involves extensive molecular manipulation of the cells under study and runs the risk of insertional mutagenesis; (ii) immune reactions may be induced; (iii) uncertainties regarding the robustness of the signal remain, as the detected signal could reflect magnitude of transgene expression instead of cell survival; (iv) gene modification adds additional cost; and (v) regulatory roadblocks. (Frangioni, et al. 2004 *Circulation* 110: 3378-3384.)

To date, most stem cell tracking studies have used direct in vitro cell labeling with SPIO followed by in vivo MRI (e.g., neural stem cells were tracked in vivo for up to 18 weeks. (Guzman, et al. 2007 *PNAS* (USA) 104, 11915-11920.) Despite the significant advantages of MRI (25-100 μm resolution, excellent anatomical and functional data), it has been found that iron-derived signals can persist in organs (e.g., myocardium) and can be detected by MRI long after the cells have been destroyed, thus generating false-positive signals. (Wang, et al. 2008 *British J. Radiology* 81: 987-988; Terrovitis, et al. 2008 *Circulation* 117: 1555-62.) SPIO labeling was also found to affect SC migration. (Schafer, et al. 2009 *Cytotherapy* 11 (1): 68-78.) Another significant clinical problem common to all MRI methods is that certain implantable devices such as pacemakers and defibrillators, are currently contraindications to MRI.

Nuclear imaging techniques, single-photon emission computed tomography (SPECT) and positron emission tomography (PET), offer high sensitivity ($10^{-11}$M-$10^{-12}$M tracer) deep in tissue. Specialized systems of both PET and SPECT allow small animal imaging with much improved spatial resolution (1-2 mm). SPECT imaging provides 3D information and can be applied both in small animals as well as in humans. Although the sensitivity of PET is 1-2 orders of magnitude better than SPECT, SPECT is less expensive, more widely available, and allows multispectral detection and uses isotopes with longer half-lives. (Stodilka, et al. 2006 *Phys. Med. Biol.* 51: 2619-2632.)

Optical imaging is a relatively new imaging modality that offers real-time, non-radioactive, and depending on the technique, high-resolution imaging of fluorochromes embedded in diseased tissues, e.g., cellular resolution is possible using microscopy techniques. Far red (FR) and near infrared (NIR)(650-900 nm wavelengths) fluorescence-based imaging is of particular interest for noninvasive in vivo imaging because of the relatively low tissue absorption, scatter, and minimal autofluorescence of FR/NIR light. The sensitivity of this modality is comparable to nuclear techniques approaching a few thousand cells and the acquisition time is quite fast, obtaining images in seconds in most cases. (Zhang, et al. 2005 *Bioconjugate Chem.* 16: 1232-1239.)

Current radioisotope and optical probes for stem cell tracking have limitations. Direct cell labeling has previously been used for early tracking of transplanted stem cells into the myocardium in clinical trials. The most widely used reporter gene for nuclear imaging is HSV-tk based PET imaging using [$^{18}$F]-FHBG as the reporter probe. HSV-tk has the additional property of serving as a suicide gene upon administration of ganciclovir, thereby allowing selective ablation of stem cell misbehavior. However, this approach suffers from many of the same limitations previously mentioned.

Direct radiolabeling of cells has traditionally been accomplished with the incorporation of lipophilic chelates: $^{111}$In-oxine, $^{111}$In-tropolone, or $^{99m}$Tc-HMPAO (hexamethylpropylene amine oxime). For stem cell tracking, the short radiological half-life of $^{99m}$Tc (6.02 h) is not particularly useful for longer term imaging studies using the direct radiolabeling approach. MSCs and endothelial progenitor cells (EPCs) labeled with $^{111}$In-oxine or $^{99m}$Tc-HMPAO have been monitored in vivo using SPECT in animal studies (e.g., radiolabeling of progenitor cells with $^{111}$In is feasible for monitoring myocardial homing and biodistribution in rats over 24-48 h. (Brenner, et al. 2004 *J. Nucl. Med.* 45 (3): 512-518.)

One problem reported with cells labeled with $^{111}$In-oxine or $^{111}$In-tropolone is the potential for accumulation of the isotope in the nucleus, resulting in radiotoxicity and limiting the amount of label possible per cell. This is due to the short range of the emitted low-energy B-particles, causing severe chromosomal aberration. (ten Berge, et al. 1983 *J. Nucl. Med.* 24: 615-620.) Evidence from a number of studies has shown that radiation damage from Auger-electron emitters such as $^{111}$In can be reduced 85-fold if the nuclide is confined to the cytoplasm rather than the nucleus. (Lambert, et al. 1996 *Nucl. Med. & Biol.* 23:417-427.) If the nuclide is restricted to the cell membrane, radiation damage can be reduced 120-fold. (Hofer, K H. 1984 Microdosimetry of labeled cells. In *Blood Cells in Nuclear Medicine*, Part II (Edited by Fueger, GF), Martinus Nijhoff Publishers, Boston; 224-243.)

The cytotoxic effects of $^{111}$In on human stem cells have also been reported to be time-dependent. (Gholamrezanezhad, et al. 2009 *Nucl. Med. Commun.* 30 (3): 210-216.) Detection at the single cell level remains a formidable challenge for radionuclide probes as the ability to concentrate radioactive agents in stem cells has yet to be achieved. (Frangioni, et al. 2004 *Circulation* 110: 3378-3384.)

Another important limitation that has been reported with $^{111}$In-oxine and $^{111}$In-tropolone is the leaking of the label from the stem cell resulting in false positive signals and also high uptake in liver and kidneys. (Brenner, et al. 2004 *J. Nucl. Med.* 45 (3): 512-518; Zhou, et al. 2005 *J. Nucl. Med.* 46 (5): 816-822.) This is because binding of these compounds to intracellular structures is reversible.

SPECT has been used to track $^{111}$In-labeled transplanted progenitor cells in murine, porcine and canine models of myocardial infaction until 14 days. (Aicher, et al. 2003 *Circulation* 107, 2134-9; Chin, et al. 2003 *Nucl. Med. Commun.* 24, 1149-54; Wisenberg, et al. 2009 *J. Cardiovascular Magnetic Reson.* 11: 11-26.) Jin et al. demonstrated that stem cells can be radiolabeled with indium up to 0.14 Bq/cell without affecting viability and function, and detected as few as 3600 cells so radiolabeled by SPECT in a phantom study. (Jin, et al. 2005 *Phys. Med. Biol.* 50: 4445-4455.)

A dual modality cell labeling probe reported is $^{125}$I-PKH95. (Slezak, et al. 1991 *Nature* 352:261-262; Ford, et al. 1996 *J. Surgical Res.* 62 (1): 23-28.) The $^{125}$I-PKH95 compound contains an iodine atom, a visible fluorescent head group (em=570 nm) and two long alkyl tails that enable it to stably embed into cell membranes irreversibly. It was labeled by exchange with $^{125}$I, but with low specific activity (15-40 Ci/mmol). (Gray, et al. 1991 *J. Nucl. Med.* 32: 1092.)

The use of an iodine isotope presents practical issues. First, exchange labeling is not efficient in producing a high specific radioactivity agent. High specific-activity is necessary to minimize the total number of dye molecules associated with each cell to diminish detrimental effects on cellular integrity. Second, it is challenging to conform to a simple kit format that can be easily radiolabeled on site.

Thus, new dual- or multi-modality probes for stem cell tracking are needed. Labeling stem cells with new dual- or multi-modality probes and tracking them via noninvasive imaging techniques may hold the key to addressing critical issues associated with successful development of stem cell therapies.

SUMMARY OF THE INVENTION

The invention is based on the unexpected discovery of novel, dual- or multi-labeled molecular probes having one or more fluorophore (e.g., a far-red fluorophore), one or more radionuclide (e.g., $^{111}$In), and one or more long hydrocarbon tails (e.g., two hydrocarbon tails). The probes of the invention incorporate into the plasma membrane of a target cell where incorporated probes are stable and non-diffusible. These probes allow dual- or multi-modality imaging of stem cells, providing more accurate determination of stem cell biodistribution in vivo.

The synergistic combination of radiologic and fluorescent labels in a single molecular probe that can be securely attached to the cell membrane prevents certain problems of existing probes, such as elution of the labels from the cell. The elution issue has strained the radiologic labels for SPECT ($^{111}$In) or PET ($^{64}$Cu) alike. Since the probes are restricted to the membrane, they exhibit minimal radiotoxicity, thereby allowing for a greater number of radiolabels per cell and thus improved sensitivity.

In one aspect, the invention generally relates to a compound of the formula:

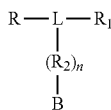

wherein

B is a chelating moiety capable of complexing to a radioactive metal;

R and $R_1$ are substituent groups independently selected from the group consisting of alkyl, alkenyl, alkynyl, alkaryl and aralkyl, each of R and $R_1$ comprising one or more linear or branched hydrocarbon chains having from 2 to about 30 carbon atoms, and each of R and $R_1$ being unsubstituted or substituted with one or more non-polar functional groups;

L comprises a fluorophore with emission in the range from about 650 nm to about 850 nm;

$R_2$ is a spacer moiety having the formula:

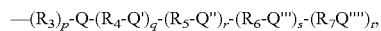

wherein $R_3$ is an aliphatic hydrocarbon, $R_4$, $R_5$, $R_6$ and $R_7$ are independently selected from the group consisting of aliphatic, alicyclic or aromatic hydrocarbons, heterocycles or $CH_2C(CO_2H)=CH$, Q, Q', Q'', Q''' and Q'''' are linking groups independently selected from the group consisting of amide, thiourea, hydrazone, acylhydrazone, ketal, acetal, orthoester, ester, anhydride, disulfide, urea, carbamate, imine, amine, ether, carbonate, thioether, sulfonamide, carbonyl, amidine and triazine, a valence bond, the aliphatic or alicyclic hydrocarbons having from about 1 to about 12 linear carbon atoms, and the aromatic hydrocarbons having from about 6 to about 12 carbon atoms;
p, q, r, s and t each is 0 or 1; and
n is 0 or 1.

In certain preferred embodiments, B is complexed to $^{111}$In ion.

In another aspect, the invention generally relates to a compound having the formula:

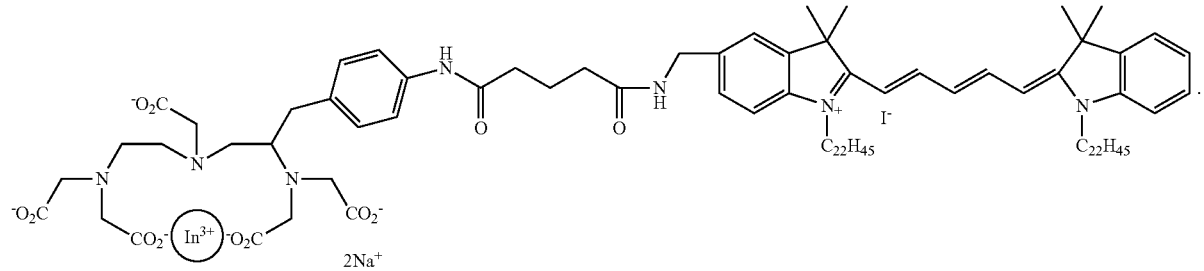

In yet another aspect, the invention generally relates to a compound having the formula:

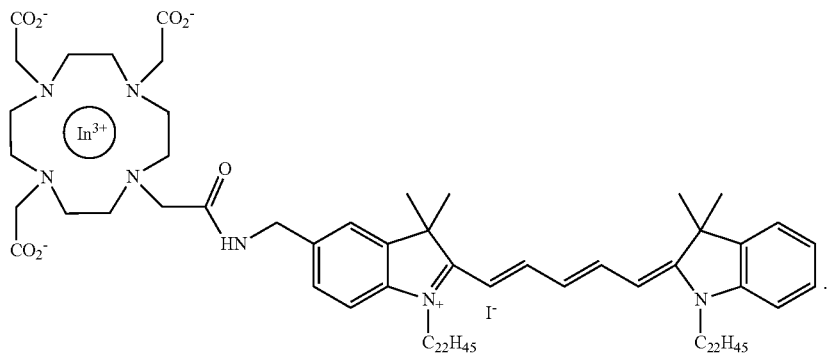

In yet another aspect, the invention generally relates to a method for imaging, tracking and/or analyzing cells. The method includes: labeling a sample of cells with a compound of the invention; and imaging the cells via two or more modalities comprising optical imaging and radiological imaging. In certain preferred embodiments, the cells are stem cells.

BRIEF DESCRIPT OF THE DRAWINGS

FIG. 1. Chemical structure of MTTI-157.

Figure 2:
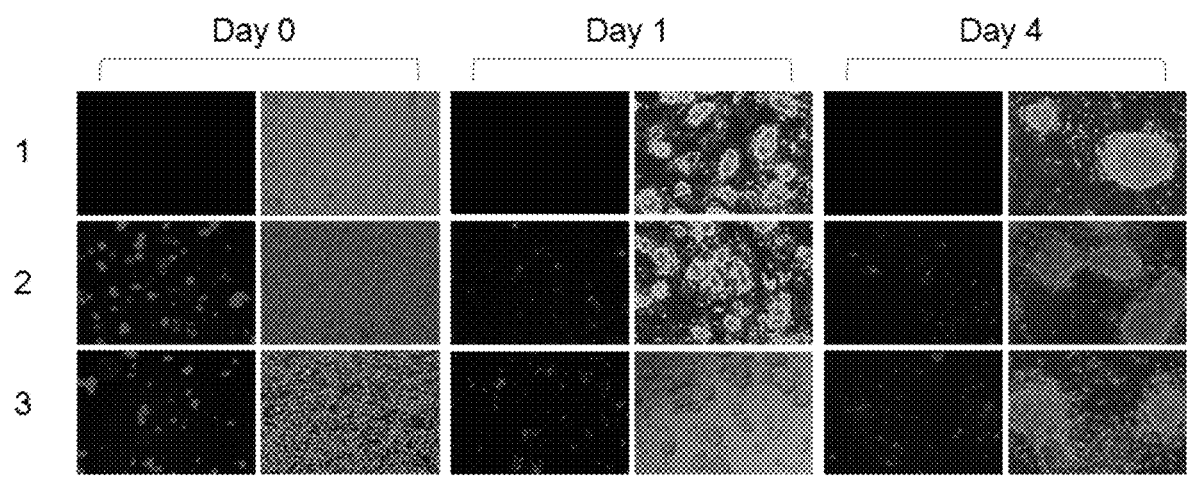

FIG. 2. Fluorescence microscopy of TC1 wild type mES cells labeled with MTTI-157 at 2 μM (Row 2) and 10 μM (Row 3) on Days 0, 1 and 4 after labeling and seeding. Unlabeled normal TC1 wild type mES cells were used as control (Row 1). Magnification: 100×.

Figure 3:
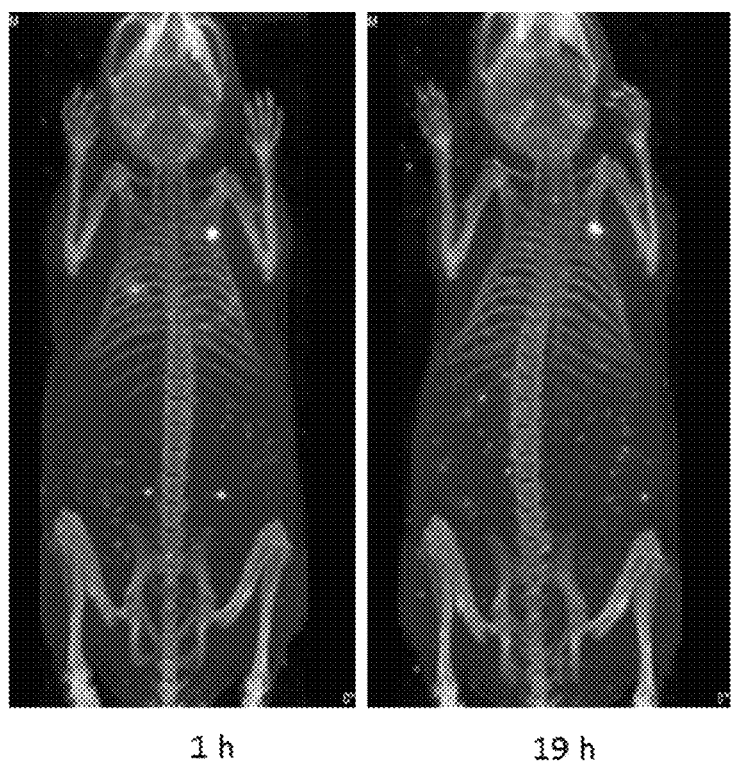

FIG. 3. SPECT/CT image of mouse injected with $^{111}$In-MTTI-157 labeled stem cells by tail vein at 1 h and 19 h after injection.

Figure 4:
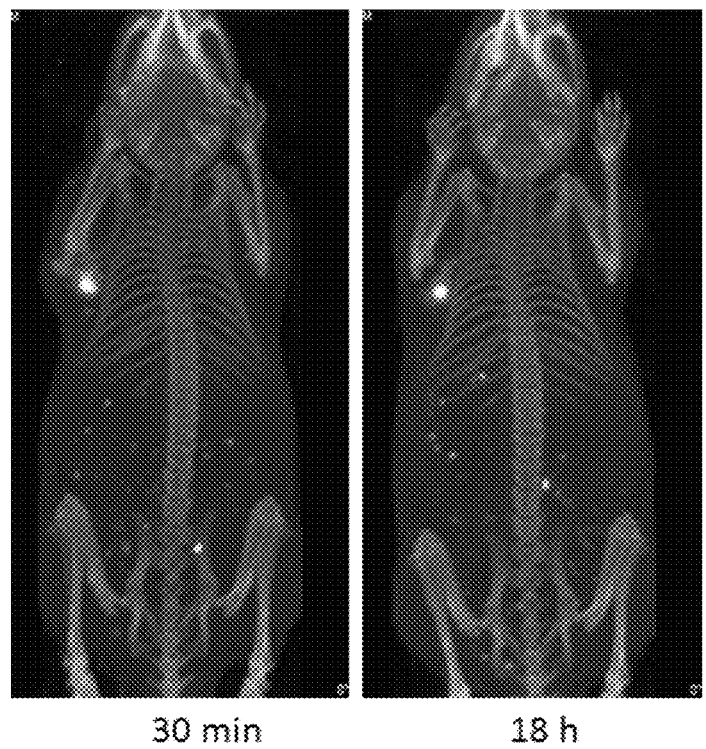

FIG. 4. Mouse SPECT/CT images at 30 min and 18 h after subq injection of $^{111}$In-MTTI-157 labeled stem cells on the shoulder.

Figure 5:
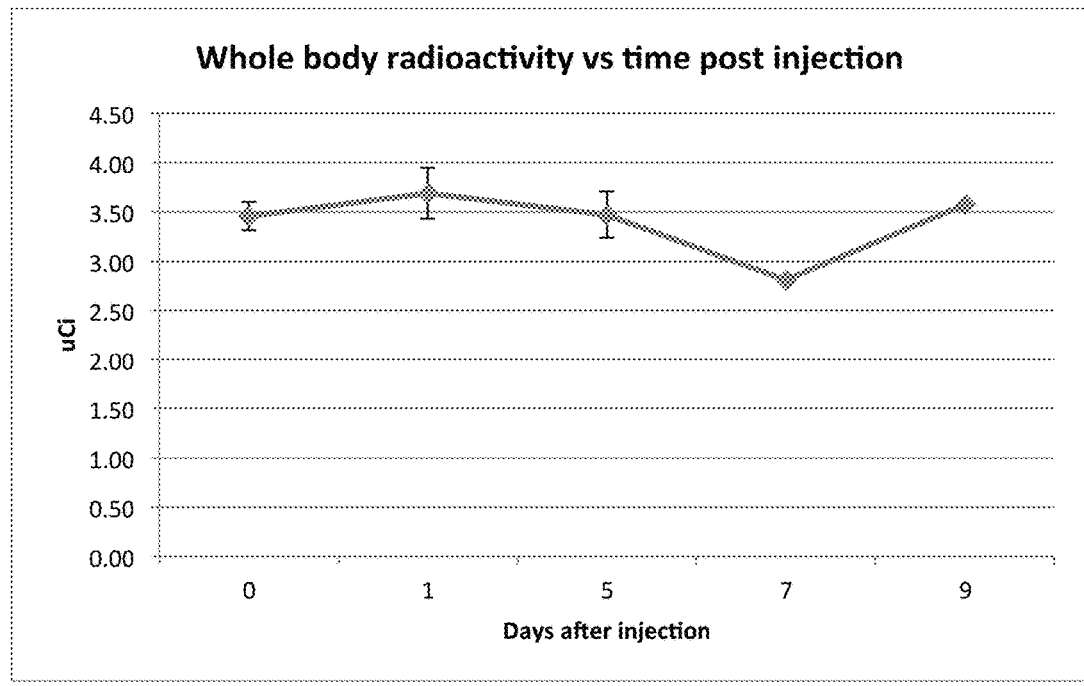

FIG. 5. Whole body count through day 9 after injection of $^{111}$In-MTTI-157 labeled stem cells by tail vain and subcutaneously on the shoulder. Corrected for decay.

Figure 6:
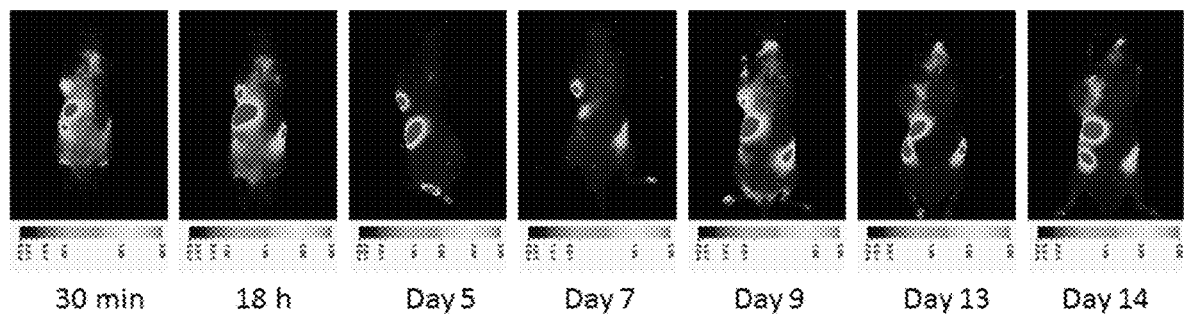

FIG. 6. Optical images of a mouse through day 14 after injection with $^{111}$In-MTTI-157 labeled stem cells subcutaneously on the left shoulder.

Figure 7:
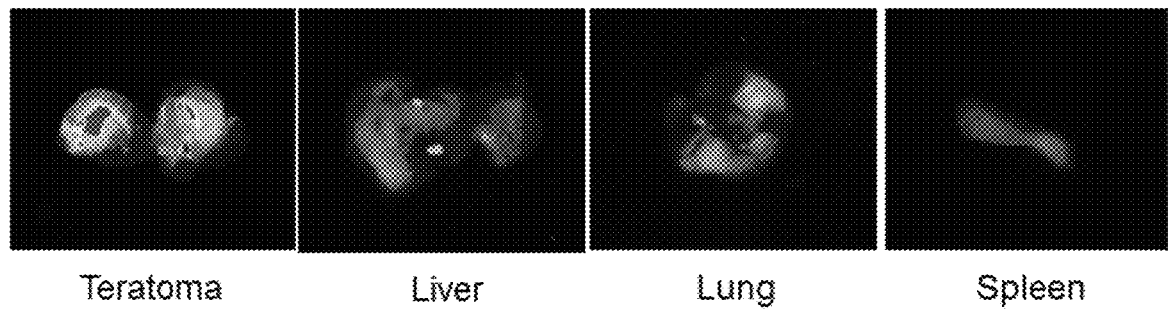

FIG. 7. Optical images of teratoma from mouse injected subcutaneously on the shoulder, liver, lung and spleen from mouse injected by tail vein.

Figure 8:
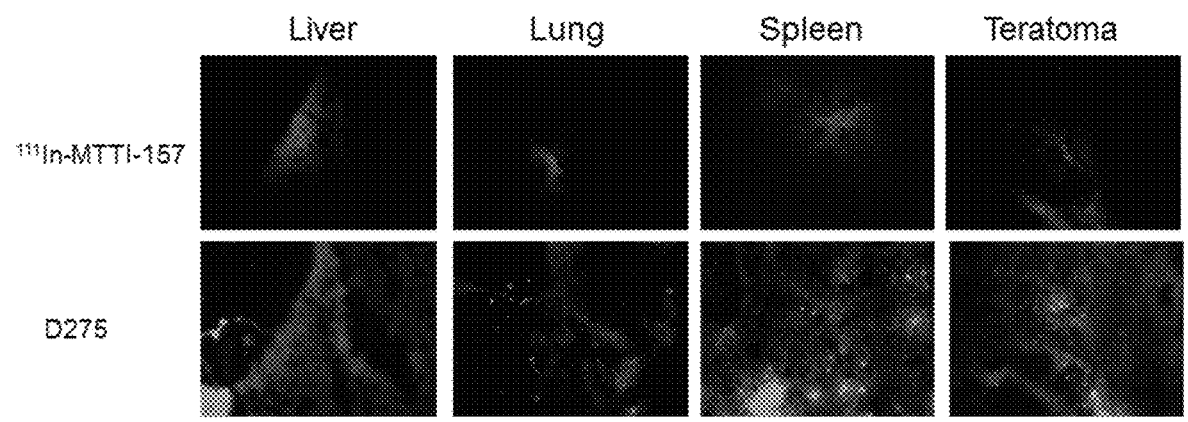

FIG. 8. Fluorescence microscopy of frozen sections from liver, lung, and spleen from a mouse sacrificed on day 10 after injection by tail vein of $^{111}$In-MTTI-157 labeled stem cells, and a teratoma from mouse on day 14 with subcutaneous injection on the shoulder. The first row, red fluorescence is $^{111}$In-MTTI-157; the second row, green fluorescence is dye D275 (Ex: 484 nm, Em: 501 nm) which was used here to stain the field of view. Magnification: 200×.

Figure 9:
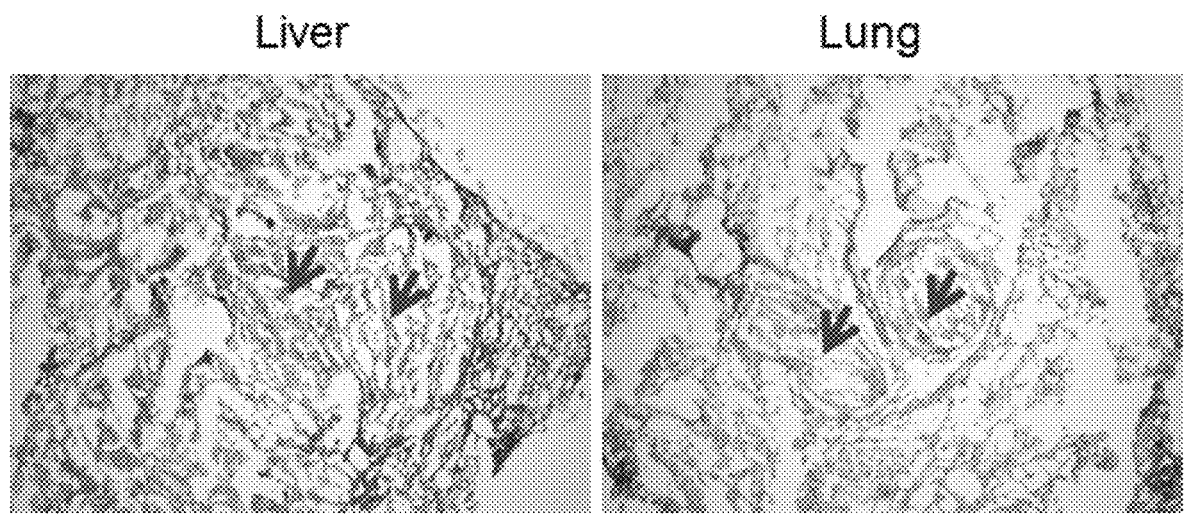

FIG. 9. H&E staining of frozen sections from liver and lungs from mouse after injection by tail vein of $^{111}$In-MTTI-157 labeled stem cells. The red arrow shows the teratoma in the sections. Magnification: 100×.

Figure 10:
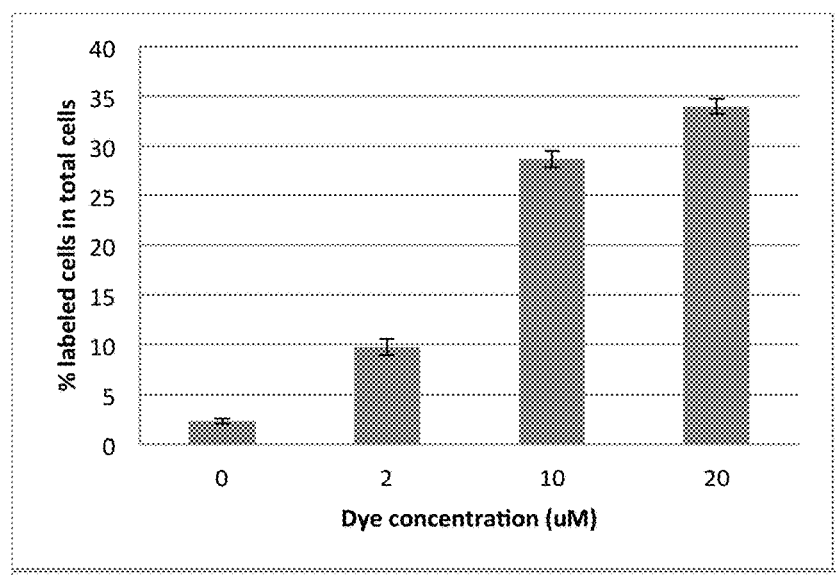

FIG. 10. Flow cytometry analysis of mES cells B/L 6 labeled with MTTI-157 conjugated with DOTA at the concentrations of 2 μM, 10 μM and 20 μM.

Figure 11:
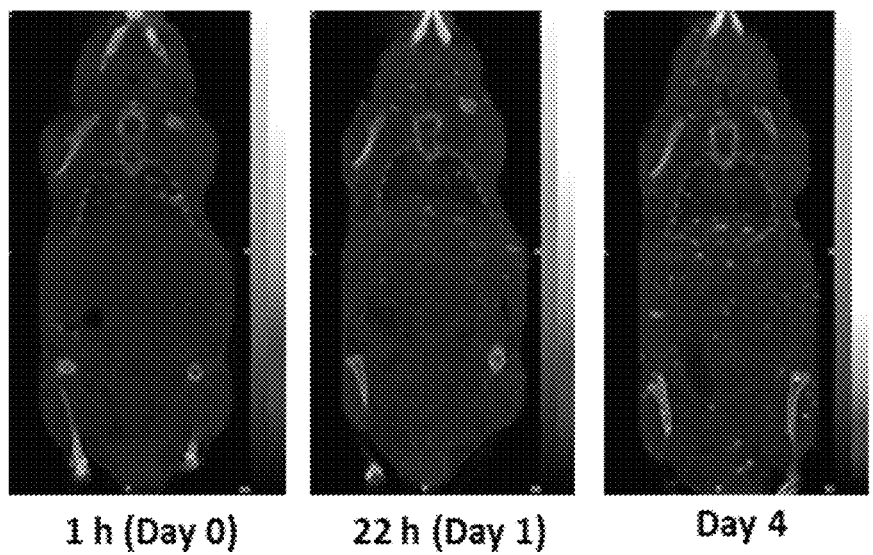

FIG. 11. SPECT/CT imaging of mouse injected $^{111}$In-MTTI-157 labeled stem cells by tail vein at 1 h, 22 h and day 4 after injection.

Figure 12:
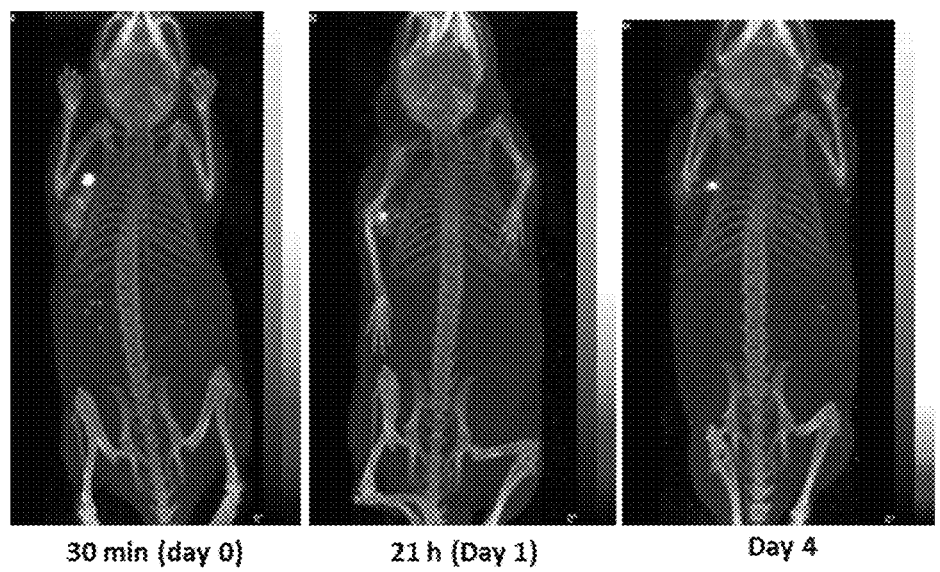

FIG. 12. SPECT/CT images of a mouse injected $^{111}$In-MTTI-157 labeled stem cells subcutaneously on the left shoulder. Views are from 30 min, 21 h and day 4 after injection of cells.

Figure 13:
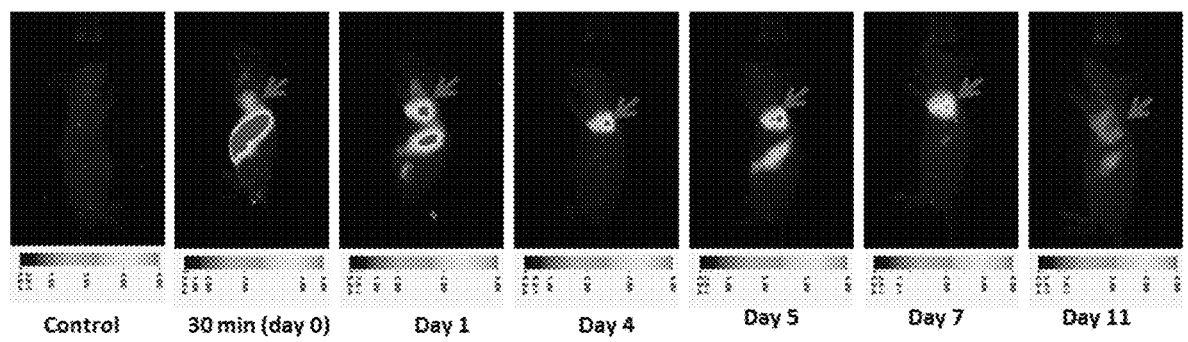

FIG. 13. Optical images of a mouse injected with $^{111}$In-MTTI-157 labeled stem cells subcutaneously on the shoulder through. Images shown are lateral views and were taken through day 11. Red arrow indicates site of cell injection site.

Figure 14:
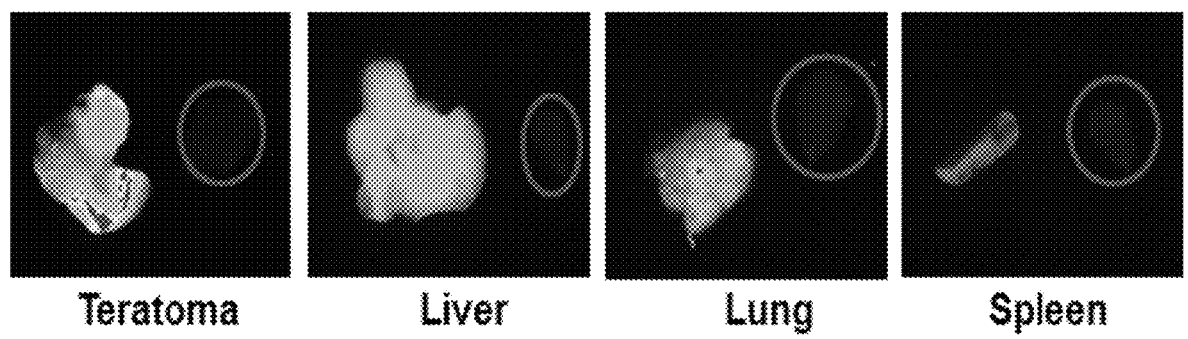

FIG. 14. Optical images of the teratoma from the mouse injected subcutaneously on the shoulder, and the liver, lung and spleen from the mouse injected by tail vein. Red circle shows the muscle in the field for background signal.

Figure 15:
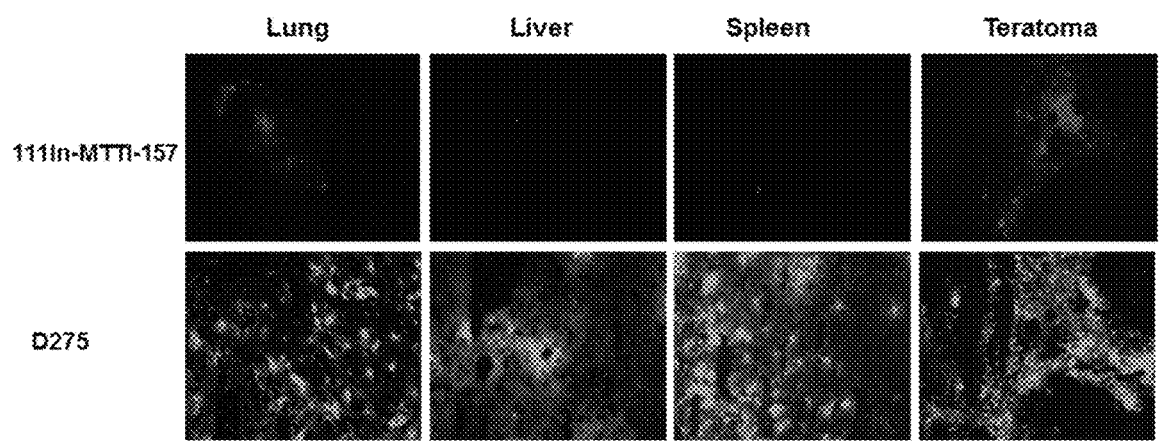

FIG. 15. Fluorescence microscopy of frozen sections from liver, lung, and spleen from mouse with iv tail injection. The teratoma is from the subcutaneous injection. The top row, red fluorescence is $^{111}$In-MTTI-157; the bottom row, green fluorescence is dye D275 (Ex: 484 nm, Em: 501 nm) which stained the cell membrane and was used here to stain the field of view. Magnification: 100×.

Figure 16:
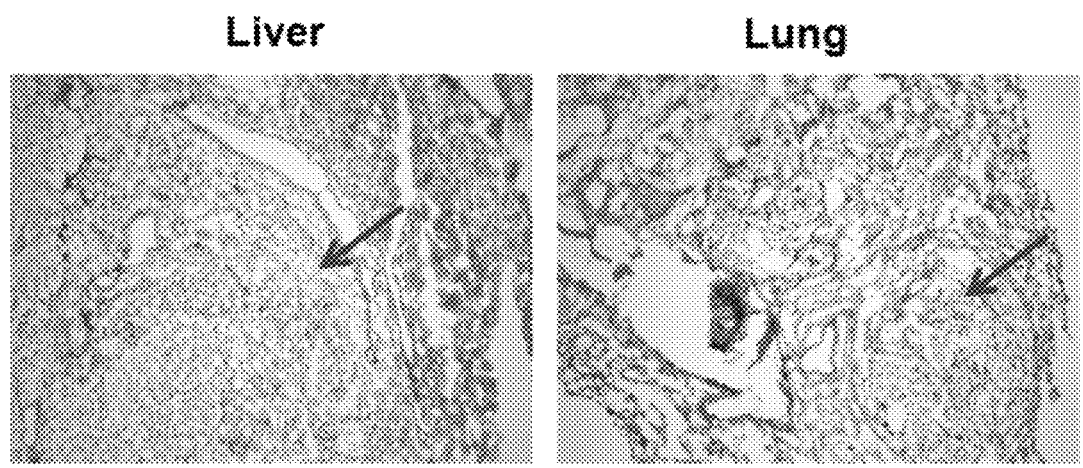

FIG. 16. H&E staining of frozen sections from liver and lungs. The red arrow indicates the teratoma within the tissue sections. Magnification: 100×.

Figure 17:
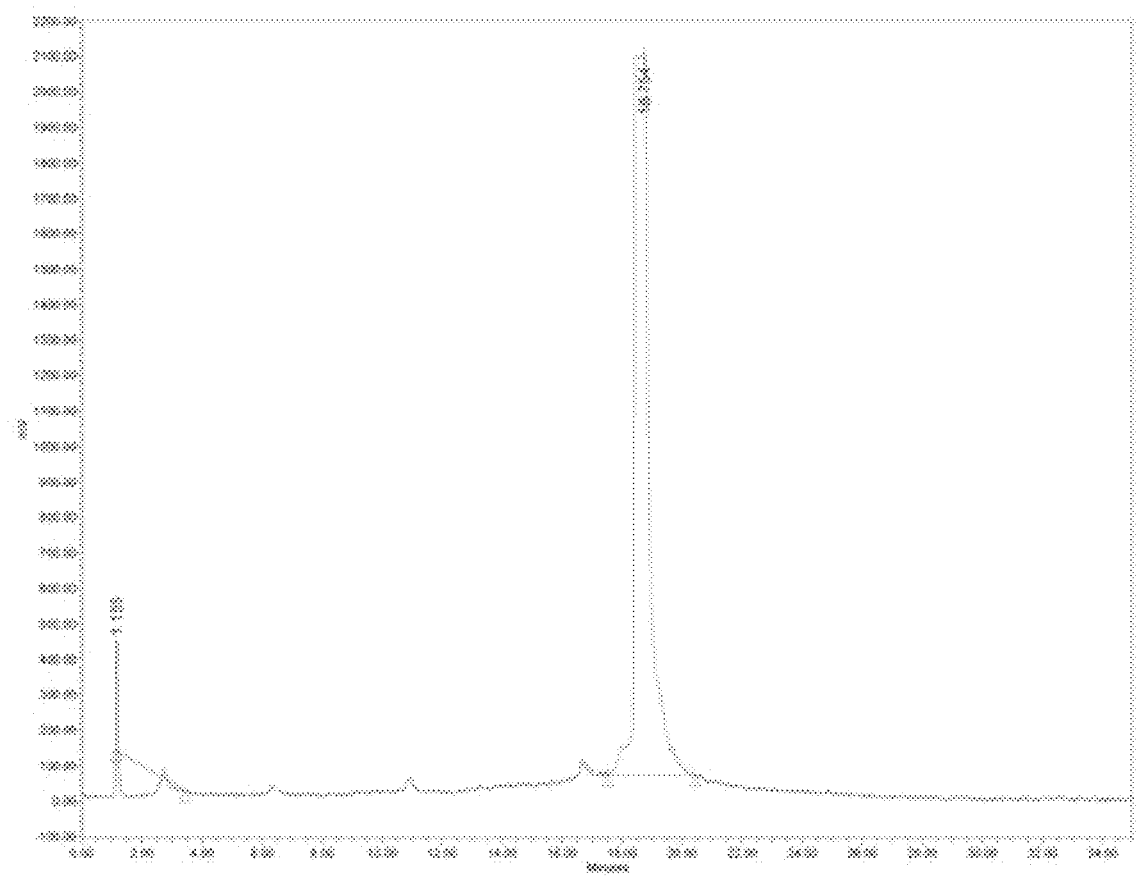

FIG. 17. C8 HPLC of $^{111}$In-MTTI-157 the product eluted at 18 min as one major peak. The labeling efficiency was greater than 90%.

Figure 18:
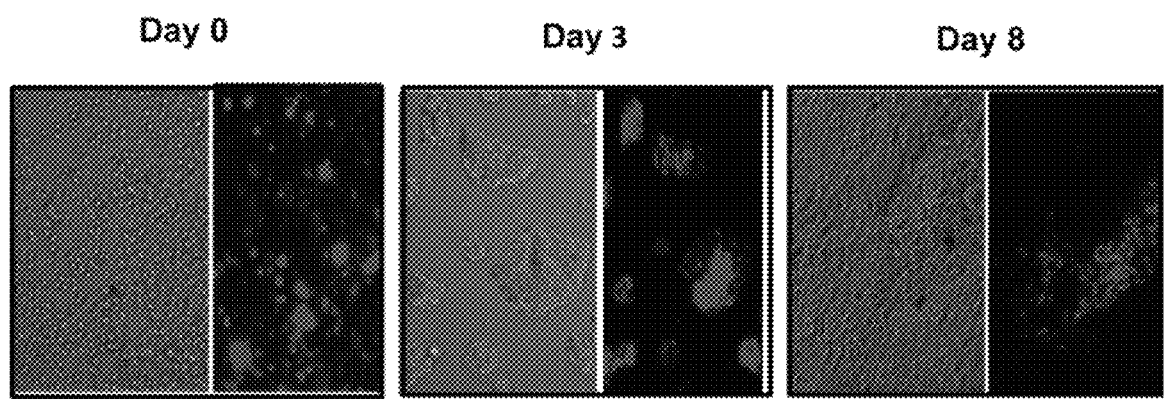

FIG. 18. The results of bright light and fluorescence microscopy of cells labeled with 20 µM $^{111}$In-MTTI-157 are shown for days 0, 3 and 8.

Figure 19:
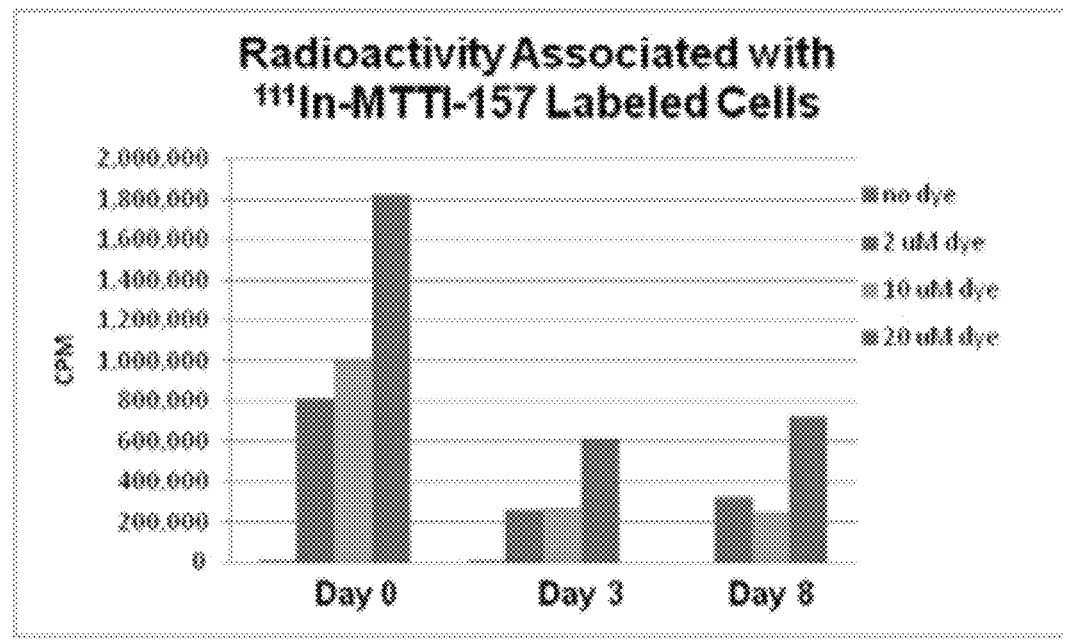
Figure 19:
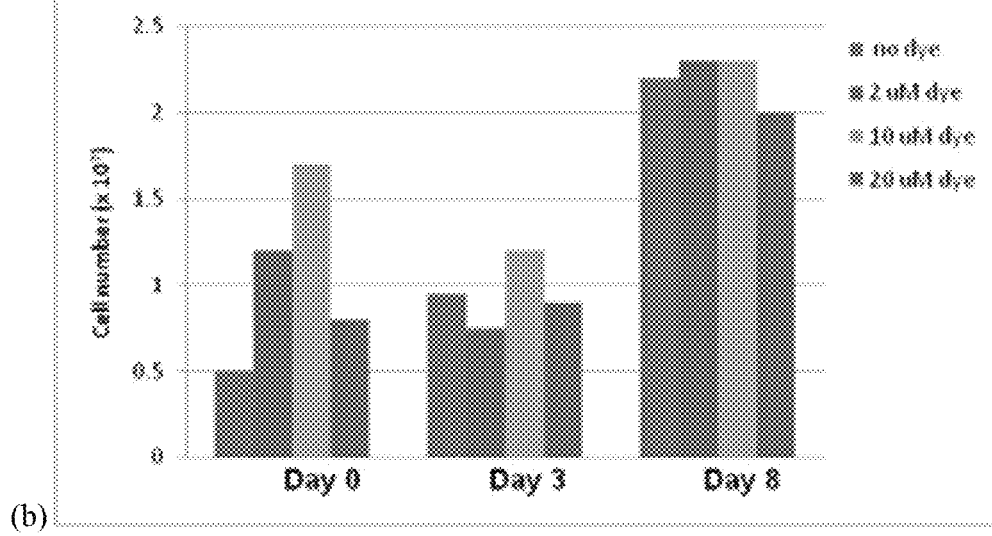

FIG. 19. The radioactivity associated with cells incubated with 2, 10 and 20 µm $^{111}$In-MTTI-157 for days 0, 3, 8, and cell growth over 8 days.

Figure 20:
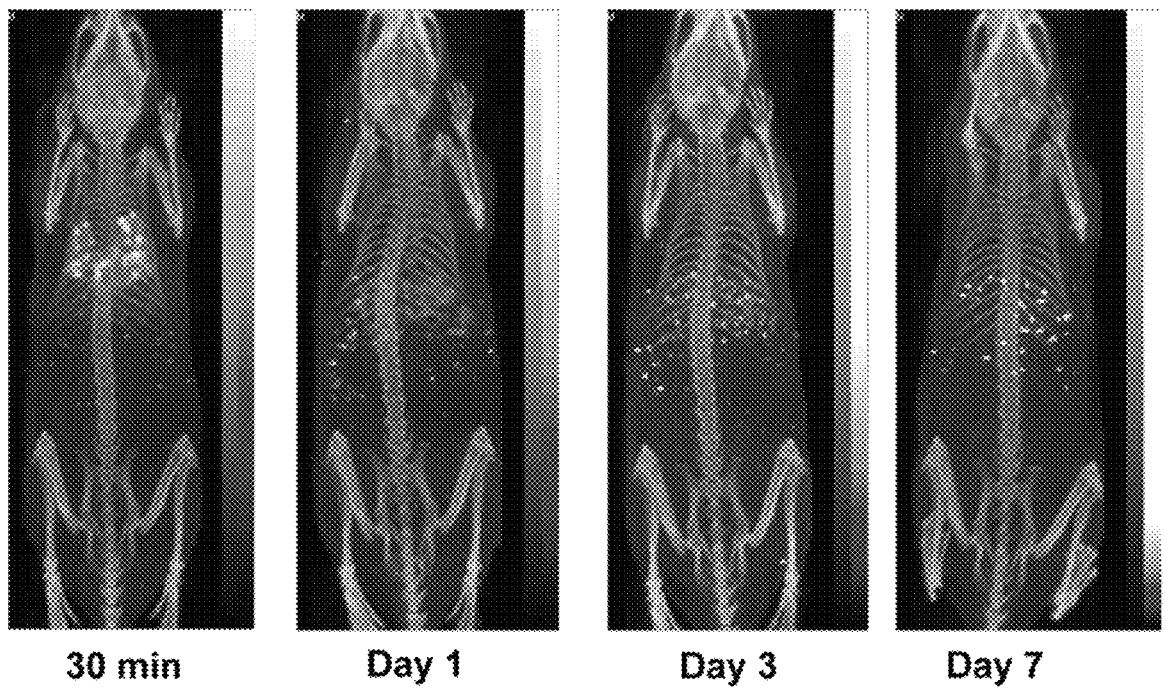
Figure 20:
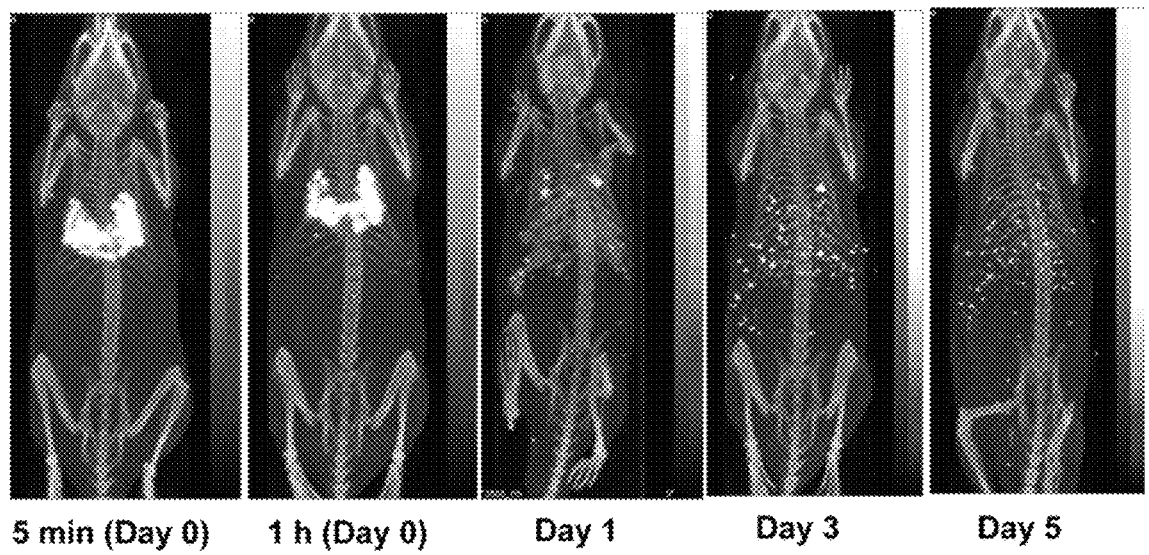

FIG. 20. $^{111}$In-MTTI-157 labeled cells (12-14 µCi on 2×10$^6$ cells) were injected IV into SKH-1 mice. Radioactivity was observed by SPECT/CT through day 7 in (a) and through day 5 (b). Activity is in the lungs in the early images and then distributes to the liver and spleen.

Figure 21:
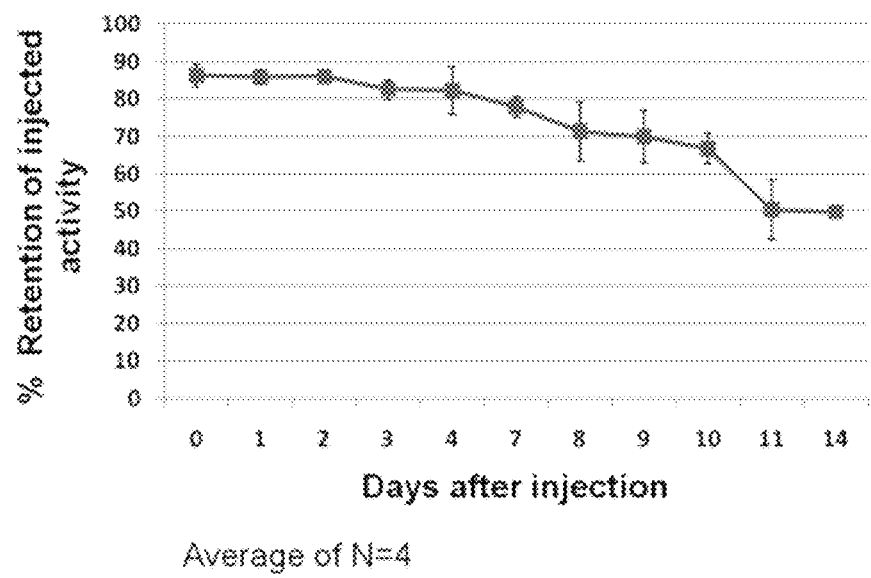

FIG. 21. Whole body $^{111}$In activity through 14 days (corrected for decay).

Figure 22:
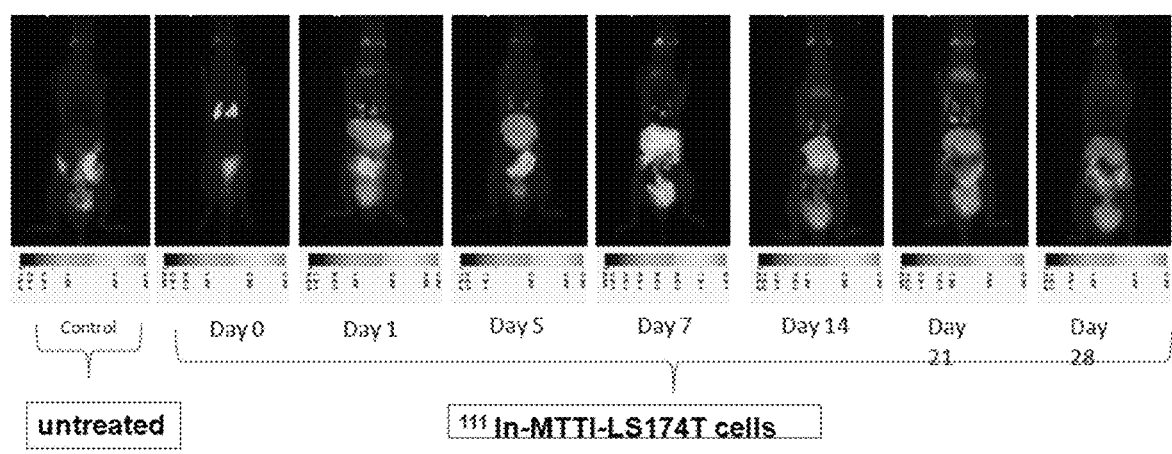

FIG. 22. Fluorescent images of SKH-1 mice (untreated, left panel); and following injection of $^{111}$In-MTTI-157 labeled cells at 5 min (day 0), and at intervals through day 28.

Figure 23:
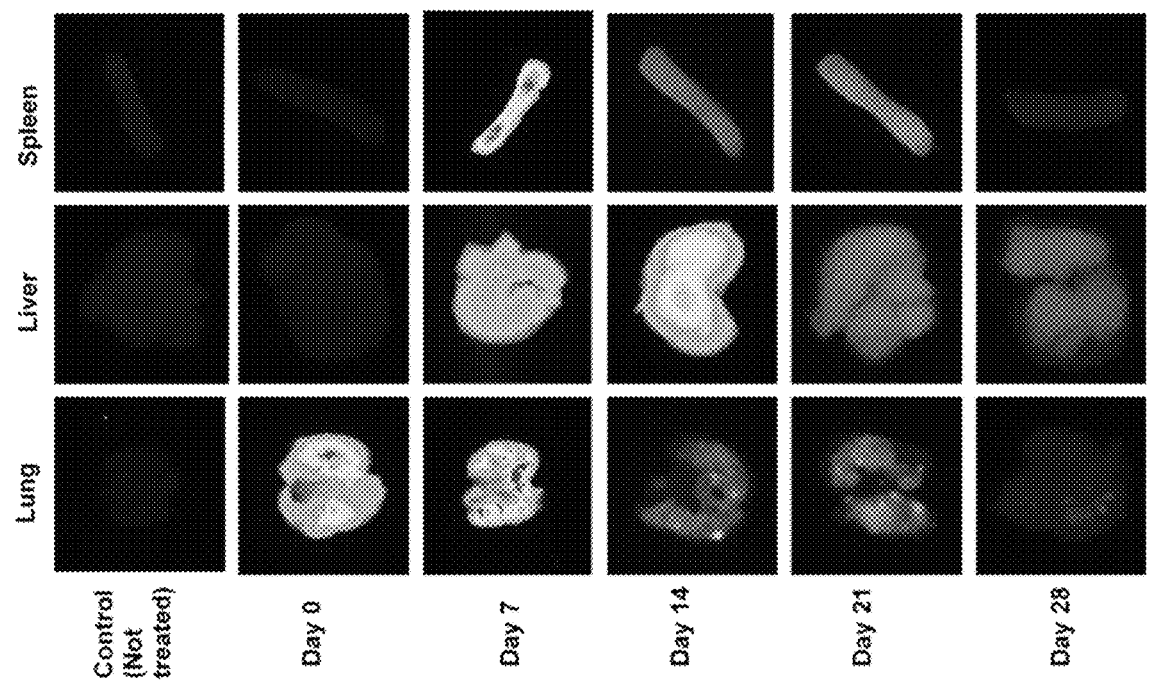

FIG. 23. Optical scans of the excised lungs, liver and spleen from mice on day 0 through day 28.

Figure 24:
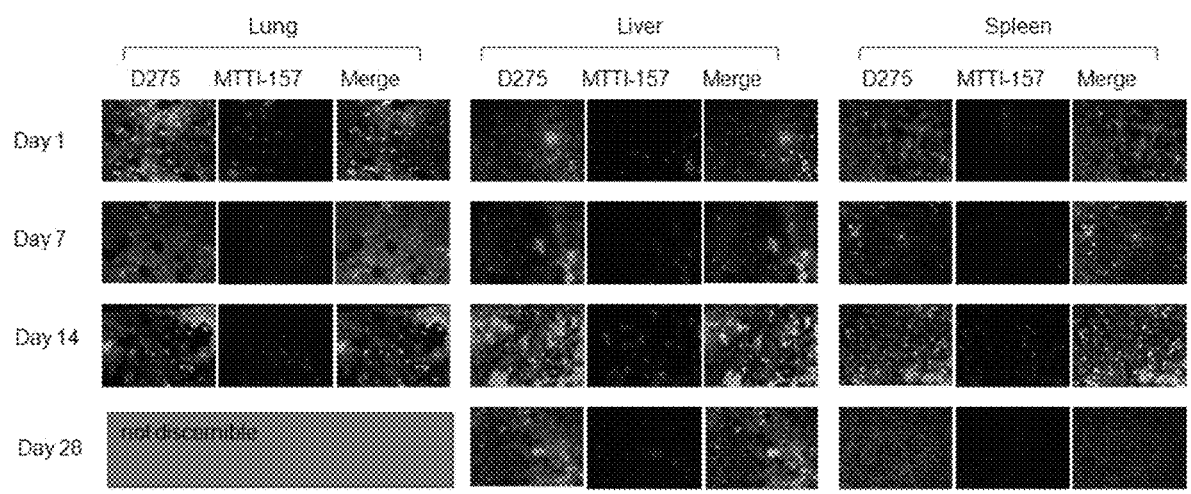

FIG. 24. Examination of lungs, liver and spleen by fluorescence microscopy confirm the retention of the MTTI-157.

Figure 25:
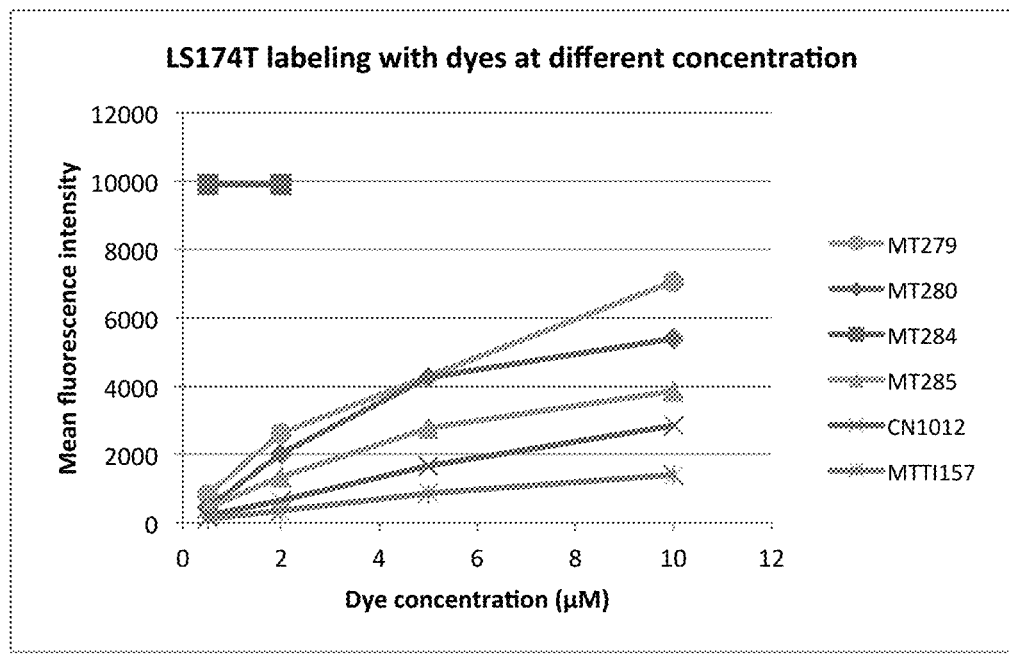

FIG. 25. Mean fluorescence intensity per cell for dyes MT279, MT280, MT284, MT285, CN1012, and MTTI-157 at different concentration.

Figure 26:
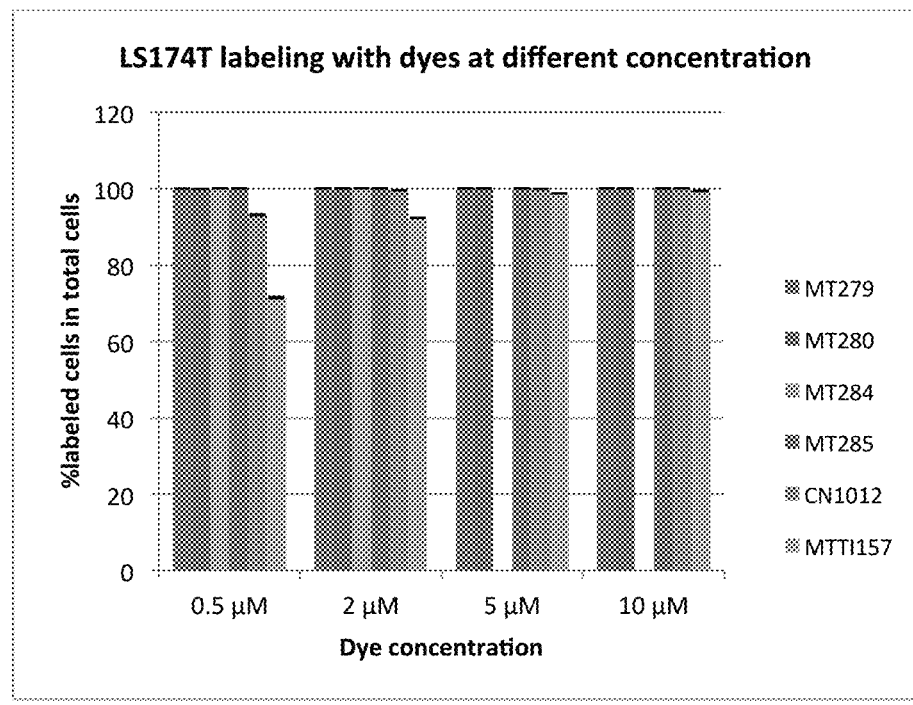

FIG. 26. Percent of cells labeled at four dye concentrations for dyes MT279, MT280, MT284, MT285, CN1012, and MTTI-157.

Figure 27:
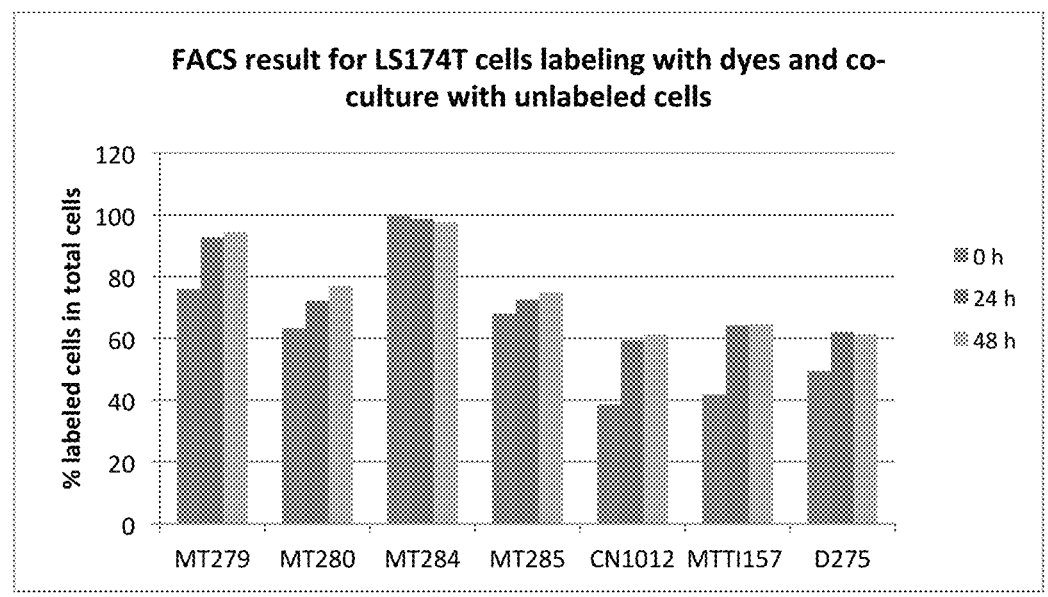

FIG. 27. Flow cytometry analysis of LS174T cells labeled with six dyes respectively and co-cultured with unlabeled cells. Percent of total cells labeled.

Figure 28:
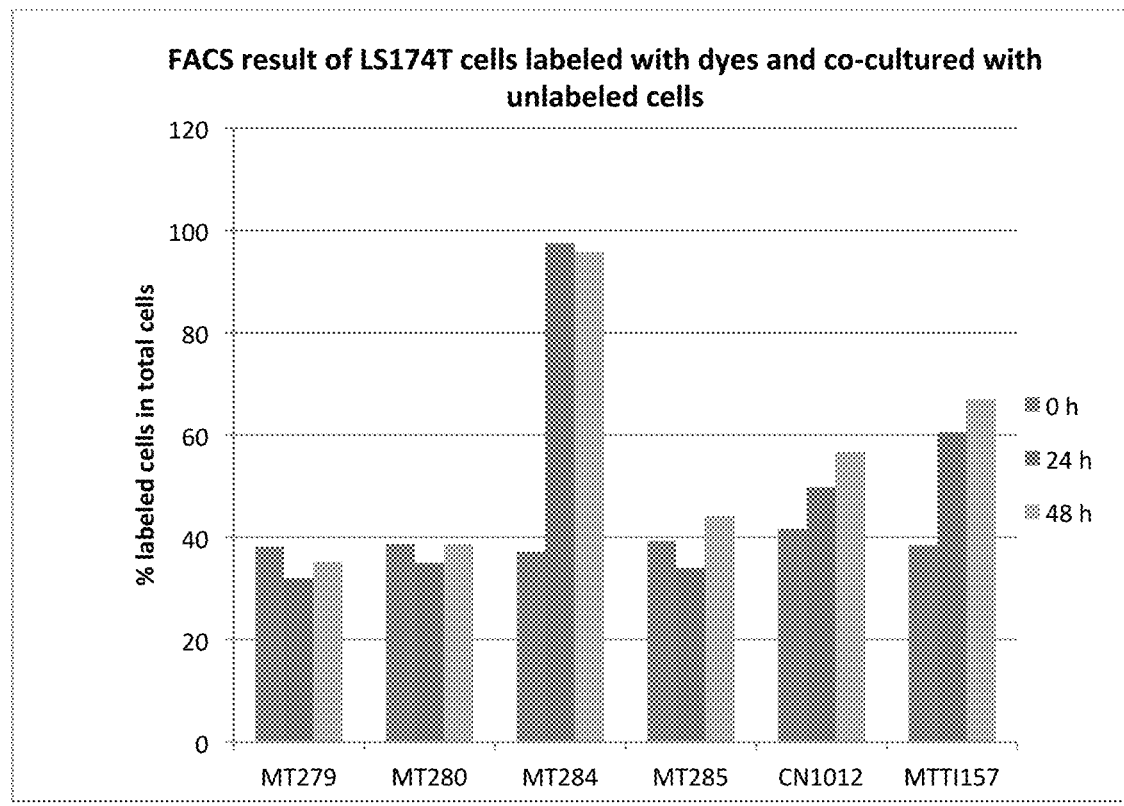

FIG. 28. Flow cytometry analysis of LS174T cells labeled with six dyes respectively and co-cultured with unlabeled cells. Percent of total cells labeled.

Figure 29:
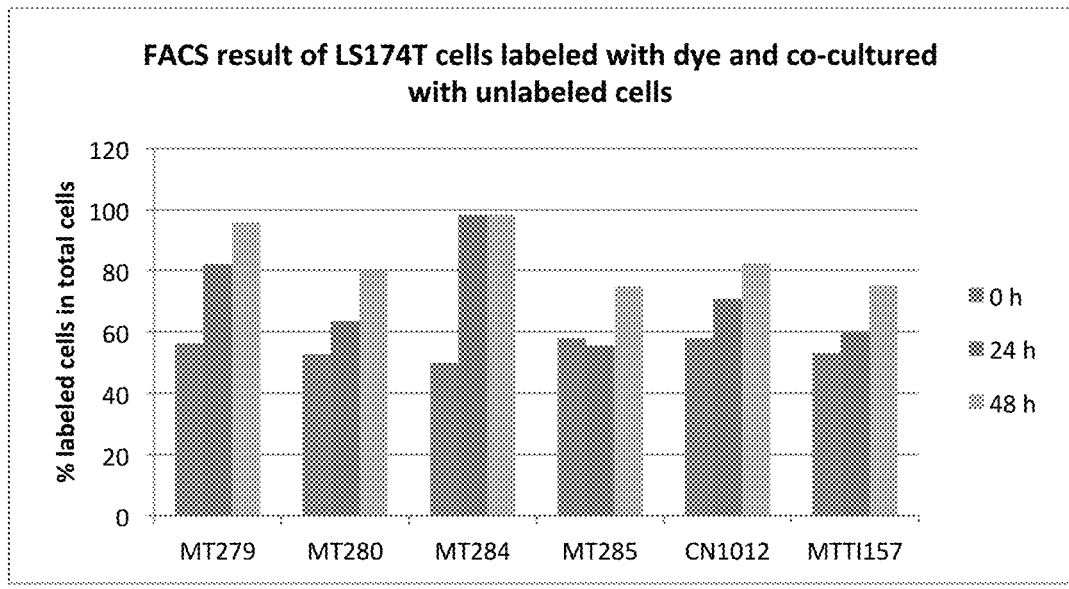

FIG. 29. Flow cytometry analysis of LS174T cells labeled with six dyes respectively and co-cultured with unlabeled cells. Percent of total cells labeled.

Figure 30:
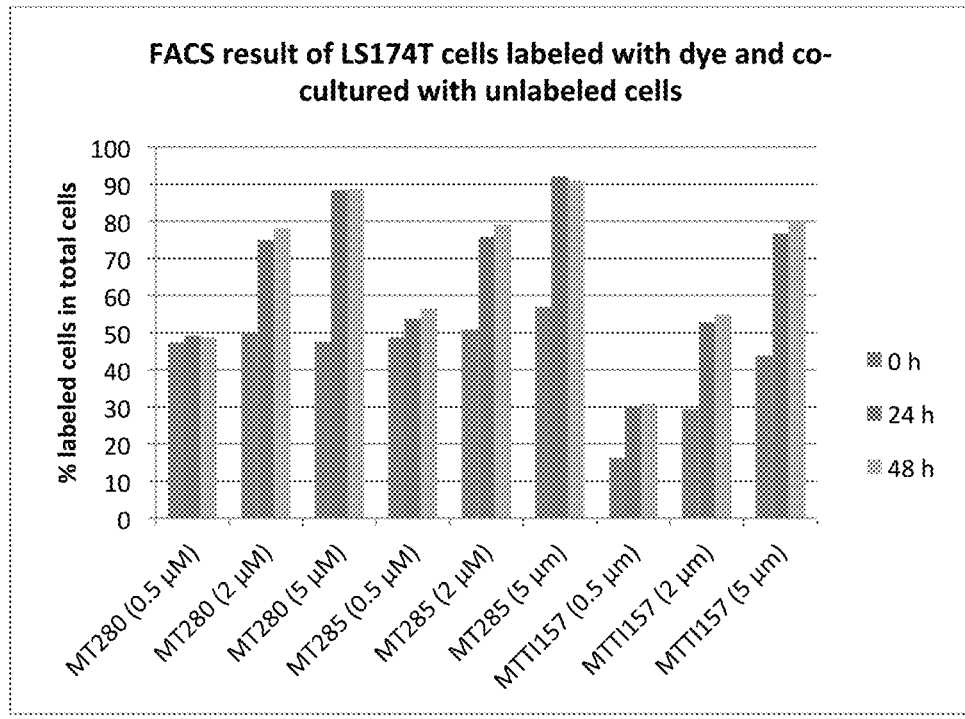

FIG. 30. Flow cytometry analysis of LS174T cells labeled with three dyes respectively and co-cultured with unlabeled cells. Percent of total cells labeled.

DEFINITIONS

Definitions of specific functional groups and chemical terms are described in more detail below. General principles of organic chemistry, as well as specific functional moieties and reactivity, are described in "Organic Chemistry", Thomas Sorrell, University Science Books, Sausalito: 2006. It will be appreciated that the compounds, as described herein, may be substituted with any number of substituents or functional moieties.

As used herein, "$C_x$-$C_y$," refers in general to groups that have from x to y (inclusive) carbon atoms. Therefore, for example, $C_1$-$C_6$ refers to groups that have 1, 2, 3, 4, 5, or 6 carbon atoms, which encompass $C_1$-$C_2$, $C_1$-$C_3$, $C_1$-$C_4$, $C_1$-$C_5$, $C_2$-$C_3$, $C_2$-$C_4$, $C_2$-$C_5$, $C_2$-$C_6$, and all like combinations. $C_1$-$C_{20}$ and the likes similarly encompass the various combinations between 1 and 20 (inclusive) carbon atoms, such as $C_1$-$C_6$, $C_1$-$C_{12}$ and $C_3$-$C_{12}$.

As used herein, the term "$C_x$-$C_y$ alkyl" refers to a saturated linear or branched free radical consisting essentially of x to y carbon atoms, wherein x is an integer from 1 to about 10 and y is an integer from about 2 to about 20. Exemplary $C_x$-$C_y$ alkyl groups include $C_1$-$C_{20}$ alkyl," which refers to a saturated linear or branched free radical consisting essentially of 1 to 20 carbon atoms and a corresponding number of hydrogen atoms. Exemplary $C_1$-$C_{20}$ alkyl groups include methyl, ethyl, n-propyl, isopropyl, n-butyl, isobutyl, dodecanyl, etc. Of course, other $C_1$-$C_{20}$ alkyl groups will be readily apparent to those of skill in the art given the benefit of the present disclosure.

As used herein, the term, "$C_x$-$C_y$ alkoxy" refers to a straight or branched chain alkyl group consisting essentially of from x to y carbon atoms that is attached to the main structure via an oxygen atom, wherein x is an integer from 1 to about 10 and y is an integer from about 2 to about 20. For example, $C_1$-$C_{20}$ alkoxy refers to a straight or branched chain alkyl group having 1-20 carbon atoms that is attached to the main structure via an oxygen atom, thus having the general formula alkyl-O—, such as, for example, methoxy, ethoxy, propoxy, isopropoxy, n-butoxy, sec-butoxy, tert-butoxy, pentoxy, 2-pentyl, isopentoxy, neopentoxy, hexoxy, 2-hexoxy, 3-hexoxy, and 3-methylpentoxy.

As used herein, the term "acyl" refers to a group or radical —C(O)R', where R' is hydrogen, alkyl, cycloalkyl, cycloheteroalkyl, aryl, arylalkyl, heteroalkyl, heteroaryl, heteroarylalkyl as defined herein. Representative examples include, but are not limited to, formyl, acetyl, cylcohexylcarbonyl, cyclohexylmethylcarbonyl, benzoyl, benzylcarbonyl and the like.

As used herein, the term "alkenyl" refers to monovalent olefinically unsaturated hydrocarbyl groups preferably having 2 to 11 carbon atoms, particularly, from 2 to 8 carbon atoms, and more particularly, from 2 to 6 carbon atoms, which can be straight-chained or branched and having at least 1 and particularly from 1 to 2 sites of olefinic unsaturation. Particular alkenyl groups include ethenyl, n-propenyl, isopropenyl, vinyl and substituted vinyl, and the like.

As used herein, the term "alkynyl" refers to acetylenically or alkynically unsaturated hydrocarbyl groups particularly having 2 to 11 carbon atoms and more particularly 2 to 6 carbon atoms which can be straight-chained or branched and having at least 1 and particularly from 1 to 2 sites of alkynyl unsaturation. Particular non-limiting examples of alkynyl groups include acetylenic, ethynyl, propargyl, and the like.

As used herein, the term "alkaryl" refers to an aryl group substituted with one or more alkyl groups.

As used herein, the term "aralkyl" refers to an alkyl group substituted with one or more aryl groups.

As used herein, the term "aryl" refers to a monovalent aromatic hydrocarbon group derived by the removal of one hydrogen atom from a single carbon atom of a parent aromatic ring system. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexylene, as-indacene, s-indacene, indane, indene, naphthalene, octacene, octaphene, octalene, ovalene, penta- 2,4-diene, pentacene, pentalene, pentaphene, perylene, phenalene, phenanthrene, picene, pleiadene, pyrene, pyranthrene, rubicene, triphenylene, trinaphthalene and the like. Particularly, an aryl group comprises from 6 to 14 carbon atoms.

As used herein, the term "halogen" refers to fluorine (F), chlorine (Cl), bromine (Br), or iodine (I).

DETAILED DESCRIPTION OF THE INVENTION

The invention generally relates to novel dual- or multi-modality probes for imaging, tracking and analyzing cells (e.g., stem cells) and related biological samples, and methods of preparation and use thereof. In particular, the molecular probes of the invention are constructed by utilizing (1) long hydrocarbon chains highly-selective for binding to plasma membranes of cells, (2) a near-infrared (NIR) dye for optical imaging, and (3) a radionuclide for PET or SPECT imaging. The in vitro and in vivo data of the optical and radiolabeled probes demonstrated their utility for detecting the presence of stem cells with multiple imaging modalities.

Stem cells are biological cells found in all multicellular organisms that can divide and differentiate into diverse specialized cell types and can self-renew to produce more stem cells. They are precursor cells that possess the capability for proliferation and self-renewal, and the ability to regenerate into multiple cell lines. Progenitor cells refer to immature or undifferentiated cells, typically found in post-natal tissues. Multiple potential sources for clinically useful stem and progenitor cells have been identified, including autologous and allogeneic embryonic cells and fetal and adult somatic cells from neural, adipose, and mesenchymal tissues. Mesenchymal stem cells (MSCs) harvested from bone marrow are easy to obtain and highly proliferative, allowing autologous transplantation without any need for immune-suppression. (Herzog, et al. 2003 *Blood* 102: 3483-3493; Jiang, et al. 2002 *Nature* 418: 41-49.) In contrast to embryo-derived stem cells, MSCs pose few ethical problems.

The development of stem cell therapies requires the ability to track cells noninvasively in vivo with agents that distribute to their daughter cells during division. For transplanted stem cells to engraft successfully cells must: (i) survive after transplant; (ii) home to the required site, (iii) differentiate into the required cell type; (iv) integrate into the desired tissue; and (v) function as the desired tissue. Alternatively, they may secrete cytokines (e.g., growth factors) that promote the growth of existing cells (i.e paracrine effect).

At present, no single imaging modality possesses all the desired qualities for optimal evaluation of stem cell therapies: (i) elucidate the optimal stem cell type and number, (ii) develop adequate administration methods, (iii) assess effects of delivery of biofactors on stem cell distribution and, (iv) evaluate stem cells as a component of tissue engineered constructs.

The novel, dual- or multi-labeled molecular probes disclosed herein have one or more fluorophore (e.g., a far-red fluorophore), one or more radionuclide (e.g., a $^{111}$In), and one or more long hydrocarbon tails (e.g., two tails). They incorporate into the plasma membrane of a cell and the incorporated probes are stable and non-diffusible.

Thus, as disclosed herein, radiologic and fluorescent labels are synergistically combined in a single molecular probe that can be securely attached to the cell membrane, providing the benefits of high sensitivity and precise anatomical localization. Since the probes are restricted to the membrane, they exhibit minimal radiotoxicity, thereby allowing for a greater number of radiolabels per cell and thus improved sensitivity. Since the probes of the invention are designed not to "leak" from the labeled stem cell they have improved accuracy in determination of stem cell biodistributions compared with $^{111}$In-oxine over a period of at least 10 days. $^{111}$In labels offer the opportunity to monitor the cells in vivo for a term of about two weeks whereas optical imaging using a membrane embedded FR/NIR fluorochrome offers the potential for possibly monitoring up to at least 16 weeks. Radiological labels allow an evaluation of sites at depth, while optical labels are useful for cells near the surface and for final single cell detection of stem cells via microscopy.

In one aspect, the invention generally relates to a compound of the formula:

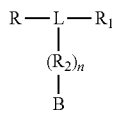

wherein

B is a chelating moiety capable of complexing to a radioactive metal;

R and $R_1$ are substituent groups independently selected from the group consisting of alkyl, alkenyl, alkynyl, alkaryl and aralkyl, each of R and $R_1$ comprising one or more linear or branched hydrocarbon chains having from about 2 to about 30 carbon atoms, and each of R and $R_1$ being unsubstituted or substituted with one or more non-polar functional groups;

L comprises a fluorophore with emission in the range from about 650 nm to about 850 nm;

$R_2$ is a spacer moiety having the formula:

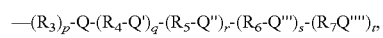

wherein $R_3$ is an aliphatic hydrocarbon, $R_4$, $R_5$, $R_6$ and $R_7$ are independently selected from the group consisting of aliphatic, alicyclic or aromatic hydrocarbons, heterocycles or $CH_2C(CO_2H)=CH$, Q, Q', Q", Q'" and Q"" are linking groups independently selected from the group consisting of amide, thiourea, hydrazone, acylhydrazone, ketal, acetal, orthoester, ester, anhydride, disulfide, urea, carbamate, imine, amine, ether, carbonate, thioether, sulfonamide, carbonyl, amidine and triazine, a valence bond, the aliphatic or alicyclic hydrocarbons having from about 1 to about 12 linear carbon atoms, and the aromatic hydrocarbons having from about 6 to about 12 carbon atoms;

p, q, r, s and t each is 0 or 1; and n is 0 or 1.

In certain preferred embodiments, B is complexed to $^{111}$In ion.

R and $R_1$ may have from about 2 to about 30 carbon atoms (e.g., from about 5 to about 30, from about 10 to about 30, from about 15 to about 30, from about 18 to about 30, from about 6 to about 25, from about 6 to about 25).

In certain preferred embodiments, the compound has the formula:

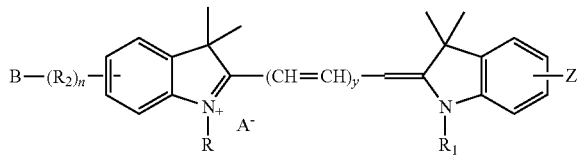

wherein
Z is a substituent selected from the group consisting of H, alkyl, OH, O-alkyl, COOH, CONH$_2$, SO$_3$H, SO$_2$NH$_2$, CONH-alkyl, CON(alkyl)$_2$, NH-acyl, NH-alkyl, N(alkyl)$_2$, SH, S-alkyl, NO$_2$, halogen, Si(alkyl)$_3$ and O—Si(alkyl)$_3$, wherein the alkyl groups independently comprising from 1 to 4 carbon atoms;
y is 2 or 3; and
A is a biologically compatible counter anion.

In certain preferred embodiments, B is complexed to $^{111}$In ion.

In certain preferred embodiments, the compound has the formula:

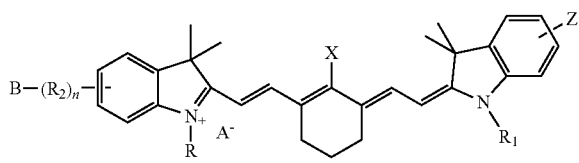

wherein
Z is a substituent selected from the group consisting of H, alkyl, OH, O-alkyl, COOH, CONH$_2$, SO$_3$H, SO$_2$NH$_2$, CONH-alkyl, CON(alkyl)$_2$, NH-acyl, NH-alkyl, N(alkyl)$_2$, SH, S-alkyl, NO$_2$, halogen, Si(alkyl)$_3$ and O—Si(alkyl)$_3$, wherein the alkyl groups independently comprising from about 1 to about 4 carbon atoms;
X is a substituent selected from the group consisting of H, halogen, phenoxy, thiophenoxy and aryl; and
A is a biologically compatible counter anion.

In certain preferred embodiments, B is complexed to $^{111}$In ion.

In certain preferred embodiments, the compound has the formula:

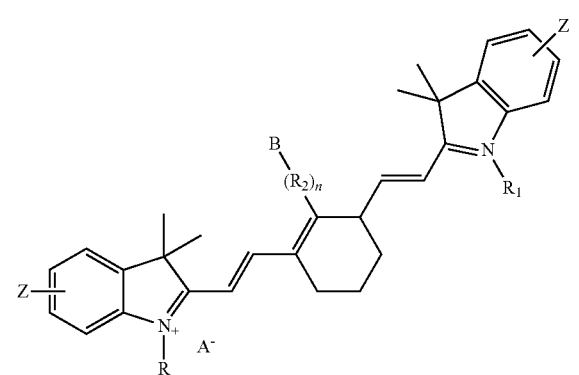

wherein
Z is a substituent selected from the group consisting of H, alkyl, OH, O-alkyl, COOH, CONH$_2$, SO$_3$H, SO$_2$NH$_2$, CONH-alkyl, CON(alkyl)$_2$, NH-acyl, NH-alkyl, N(alkyl)$_2$, SH, S-alkyl, NO$_2$, halogen, Si(alkyl)$_3$ and O—Si(alkyl)$_3$, wherein the alkyl groups independently comprising from about 1 to about 4 carbon atoms.

In certain preferred embodiments, B is complexed to $^{111}$In ion.

In certain preferred embodiments, the compound has the formula:

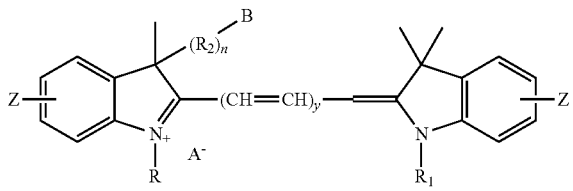

wherein
Z is a substituent selected from the group consisting of H, alkyl, OH, O-alkyl, COOH, CONH$_2$, SO$_3$H, SO$_2$NH$_2$, CONH-alkyl, CON(alkyl)$_2$, NH-acyl, NH-alkyl, N(alkyl)$_2$, SH, S-alkyl, NO$_2$, halogen, Si(alkyl)$_3$ and O—Si(alkyl)$_3$, wherein the alkyl groups independently comprising from about 1 to about 4 carbon atoms.

In certain preferred embodiments, B is complexed to $^{111}$In ion.

In certain preferred embodiments, the compound has the formula:

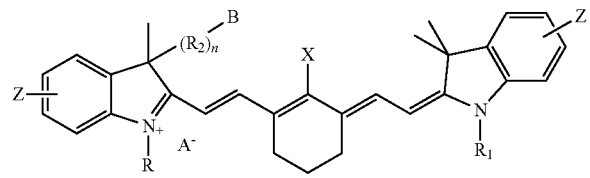

wherein
Z is a substituent selected from the group consisting of H, alkyl, OH, O-alkyl, COOH, CONH$_2$, SO$_3$H, SO$_2$NH$_2$, CONH-alkyl, CON(alkyl)$_2$, NH-acyl, NH-alkyl, N(alkyl)$_2$, SH, S-alkyl, NO$_2$, halogen, Si(alkyl)$_3$ and O—Si(alkyl)$_3$, wherein the alkyl groups independently comprising from about 1 to about 4 carbon atoms; and
X is a substituent selected from the group consisting of H, halogen, phenoxy, thiophenoxy and aryl.

In certain preferred embodiments, B is complexed to $^{111}$In ion.

In certain preferred embodiments, the compound has the formula

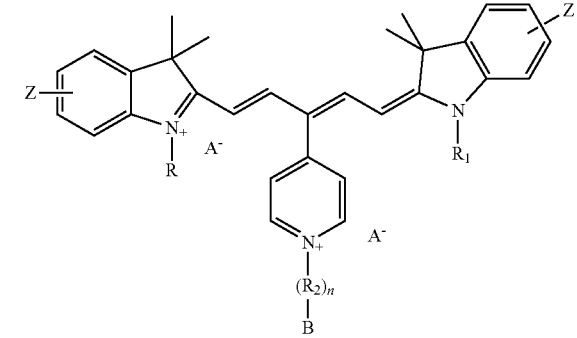

wherein

Z is a substituent selected from the group consisting of H, alkyl, OH, O-alkyl, COOH, $CONH_2$, $SO_3H$, $SO_2NH_2$, CONH-alkyl, $CON(alkyl)_2$, NH-acyl, NH-alkyl, $N(alkyl)_2$, SH, S-alkyl, $NO_2$, halogen, $Si(alkyl)_3$ and O—$Si(alkyl)_3$, wherein the alkyl groups independently comprising from about 1 to about 4 carbon atoms.

In certain preferred embodiments, B is complexed to $^{111}$In ion.

In another aspect, the invention generally relates to a compound having the formula:

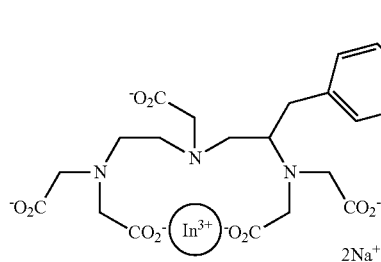
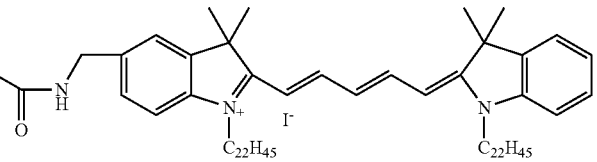

In yet another aspect, the invention generally relates to a compound having the formula:

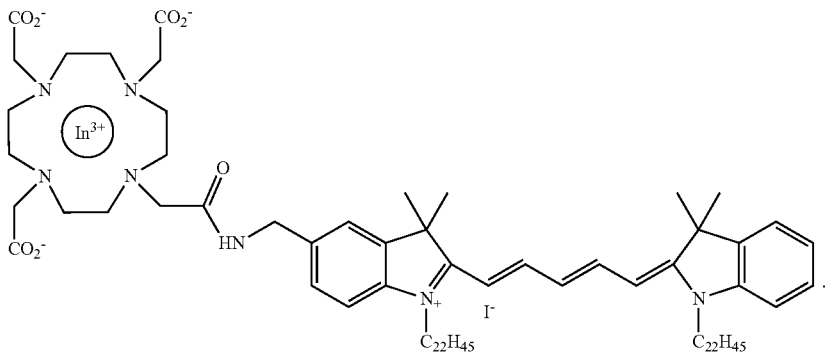

In yet another aspect, the invention generally relates to a method for imaging, tracking and/or analyzing cells. The method includes: labeling a sample of cells with a compound of the invention; and imaging the cells via two or more modalities comprising optical imaging and radiological imaging. In certain preferred embodiments, the cells are stem cells.

Dual- or multi-modality labeling probes disclosed herein also present significant commercial potential. These compounds are compatible with numerous types of instrumentation to allow wide use and quick adoption. Clinical and small animal PET and SPECT systems are widely available as are numerous small animal optical imaging systems based upon fluorescence. For example, a patient for stem cell therapy may be administered stem cells labeled with the dual imaging probe. Initially, the localization, quantification and clearance of the stem cells are visualized by whole-body nuclear imaging (SPECT/CT). At later time points, if necessary inter operative optical probes could be used to establish retention and differentiation at the disease site. Thus, the invention allows optimized preparation and labeling of stem cells ex vivo and tracking the cells in vivo once re-injected back into the patient such that there are no or minimal effects on cell viability, membrane integrity, proliferation, differentiation and function. The probes of the invention can be used for tracking stem cells in vivo as well as for use in cell based therapies.

Disclosed herein are various examples that demonstrate incorporation and stability of dye, viability of labeled cells, and ability of dye to be carried through to the subsequent generations of cells.

EXAMPLES

The DOTA (1,4,7,10-tetraazacyclododecane-1,4,7,10-tetraacetic acid) conjugated DiD fluorescent analog (fluorescence excitation 648 nm, emission 667 nm) (MTTI-157) is shown in FIG. 1).

Example 1: Preparation of Exemplary Compounds (as Shown in Scheme 1)

Preparation of Compound (1)

Compound (1) was prepared according to the procedure of Gale et al. (1977).

Preparation of Compound (2)

Compound (1) (20.6 g, 0.065 mol) and n-docosanyl-4-chlorobenzenesulfonate (32.4 g, 0.065 mol) were heated together at 130° C. with stirring for 2 h. The mixture was then cooled to RT and the crude solid recrystallized from ethyl acetate to yield pure (2) (36.4 g, 69%). $^1$H NMR ($CDCl_3$, 200 MHz): δ7.50-7.90 (m, 8H), 7.20-7.30 (m, 3H), 4.95 (s, 2H), 4.65 (t, 2H), 2.95 (s, 3H), 1.7-1.9 (m), 1.55 (s, 6H), 1.10-1.40 (m), 0.85 (t, 3H).

Preparation of compound (3)

Compound (2) (36 g, 0.044 mol) was dissolved in concentrated hydrochloric acid (660 mL) and the solution slowly heated to 115° C. over 2 h and then refluxed at this temperature for 22 h. The solution was then cooled to RT and placed in and ice bath and then taken to pH=9 with 30% ammonium hydroxide solution. The solution was diluted further with water and then extracted with dichloromethane (3×300 mL). The organic extracts were dried over magnesium sulfate, filtered and concentrated to provide the product (12.8 g, 57%). $^1$H NMR (CDCl$_3$, 200 MHz): δ 7.0-7.10 (m, 2H), 6.50 (d, 1H), 3.75-3.90 (m, 4H), 3.45 (t, 2H), 1.90 (s), 1.50-1.70 (m), 1.10-1.40 (m), 0.85 (t, 3H).

Preparation of Compound (4)

Compound (3) (12.8 g, 0.0258 mol) was dissolved in methyl formate (50 mL) and heated at reflux under an argon atmosphere for 24 h. The excess methyl formate was then removed by rotary evaporation and the crude recrystallized from hexane to provide pure material (7.62 g, 56%).

Preparation of Compound (5)

2,3,3-trimethyl-(3H)-indoleine (626 g, 0.04 mol) and n-docosanyl-4-chlorobenzene sulfonate (20.02 g, 0.04 mol) [Sondermann, 1971] were heated together at 140° C. with stirring for 3 h. The reaction was then cooled provide a waxy solid. The solid was dissolved in ethanol (250 mL) and 200 mL of saturated potassium iodide was added followed by stirring for 30 min. 1 L of cold water was added and stirring continued for another 15 min. The precipitate was collected by filtration, washed with water, dried under high vacuum and recrystallized from methylene chloride/hexane to furnish pure (5) (14.5 g, 61%), mp=107-110° C. $^1$H NMR (CDCl$_3$, 200 MHz): δ 7.50-7.80 (m, 4H), 4.65 (t, J=8 Hz, 2H), 3.10 (s, 3H), 1.80-2.00 (m, 2H), 1.65 (s, 6H), 1.10-1.50 (m), 0.85 (t, J=7 Hz, 3H).

Preparation of Compound (6)

A mixture of compound (5) (1 g, 1.68 mmol) and malonaldehyde bis(phenylimine)monohydrochloride (0.478 mg, 1.85 mmol) in acetic anhydride (40 mL) was heated at 120° C. in an oil bath for 1 h. After cooling to RT, it was added to 100 mL of 10% potasssium iodide solution and refrigerated. The solid preipitate was collected by filtration, washed with water and dried in a vacuum oven to furnish 1.5 grams of product (100% yield) which was used without further purification.

Preparation of Compound (7)

Compound (6) (1.5 g, 2 mmol) and compound (4) (1.05 g, 2 mmol) were refluxed together in dichloromethane (40 mL) for 2 h. After concentration the crude material was purified by silica gel chromatography eluting with an increasing gradient of methanol (0 to 5%) in dichloromethane. The product was further purified by recrystallization from ethanol to provide pure (7) (240 mg, 9.4%). $^1$H NMR (CDCl$_3$, 400 MHz): δ8.35 (s, 1H), 8.09-7.98 (m, 2H), 7.75-7.68 (m, 1H), 7.60 (s, 1H), 7.39 (q, 3H, J=16.3), 7.24 (t, 1H, J=7.4), 7.03 (dd, 2H, J=13.6), 6.64 (t, 1H, J=12.4), 6.16 (m, 2H), 4.55 (d, 2H, J=6.2), 4.00 (q, 4H, J=15.7), 1.50-1.21 (m, 68H), 0.883 (t, 6H, J=7.0). Expected M$^+$ (C$_{71}$H$_{118}$N$_3$O)=1028.93; Observed M$^+$=1029.0.

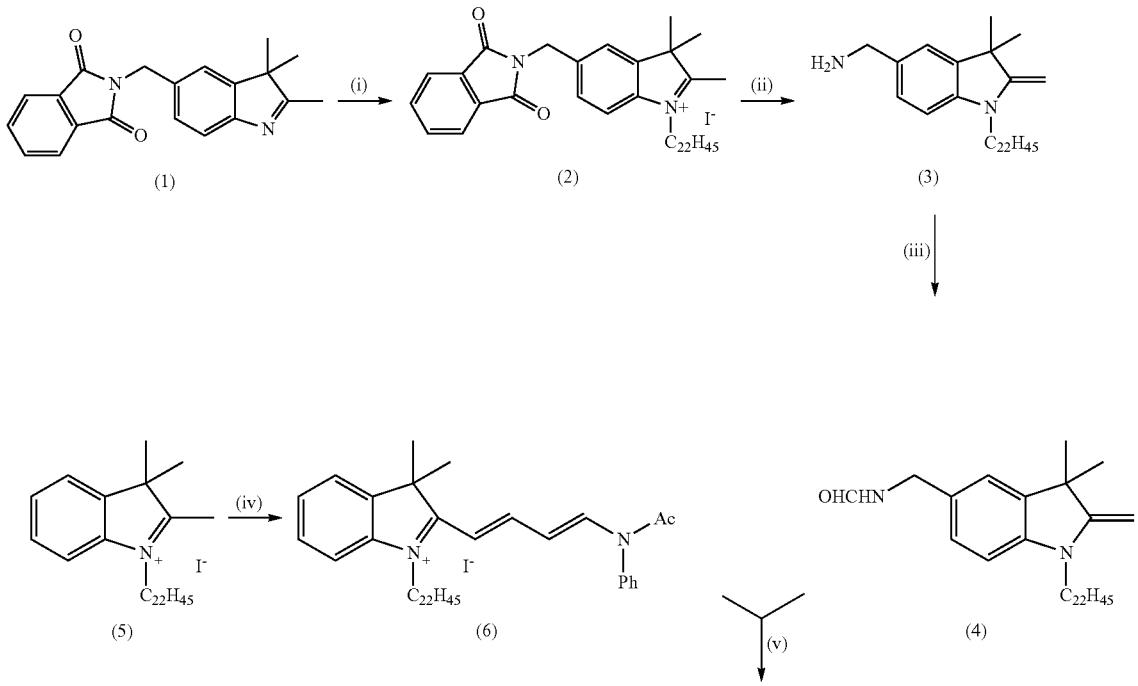

Scheme 1

-continued

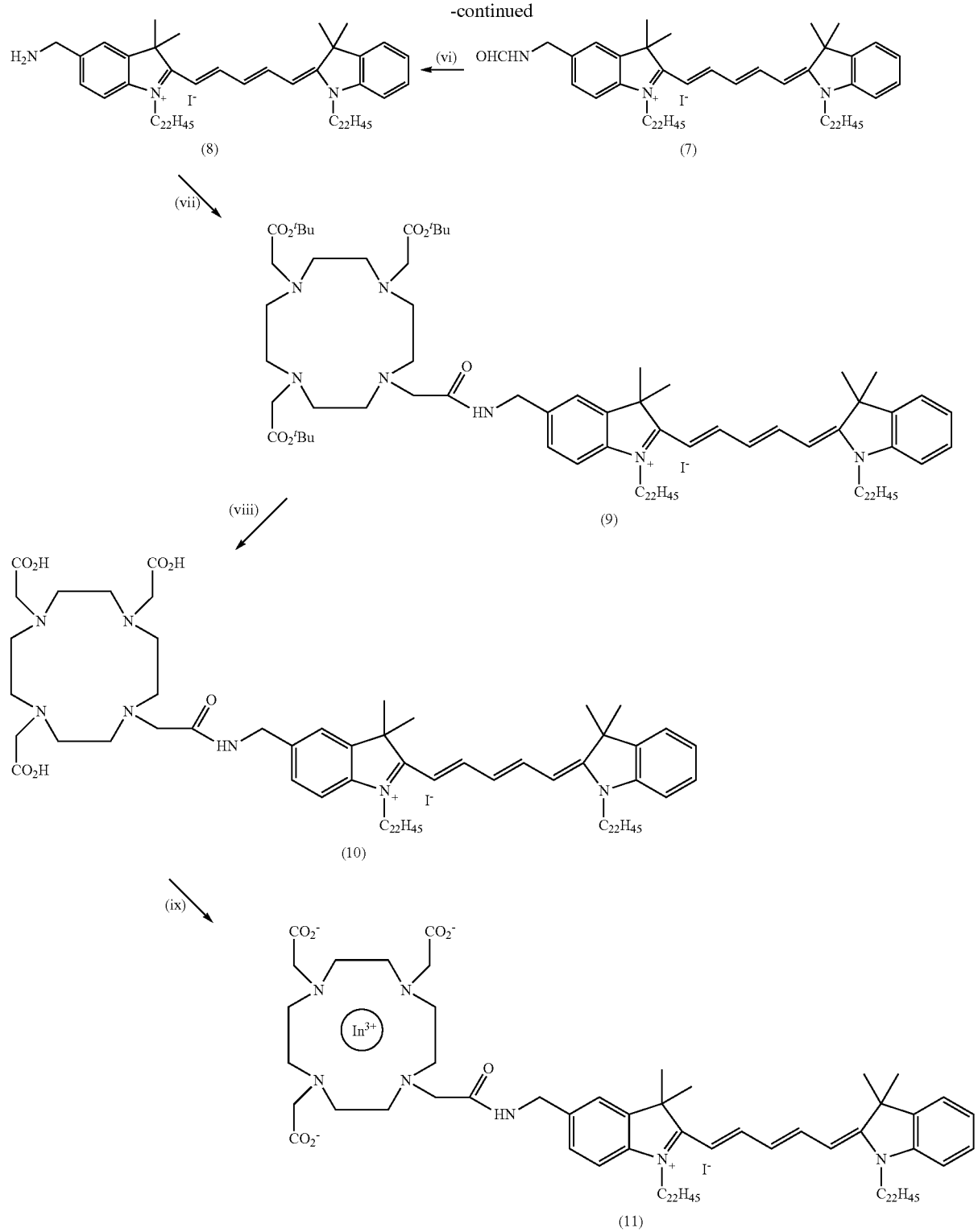

Scheme 1 is a synthetic scheme for preparing non-radioactive and radioactive indium labeled compounds of the invention with a DOTA chelator. Reagents: (i) n-docosanyl-4-chlorobenzene-sulfonate, KI (ii) cHCl, heat (iii) methylformate, heat (iv) malonaldehyde bis-(phenyl-imine) mono-hydrochloride, $Ac_2O$, heat (v) heat (vi) 47% HI (vii) DOTA-mono-NHS-tris($^t$butylester).$HPF_6$, DIPEA (viii) $TFA/CH_2Cl_2$ (60:40) (ix) EtOH, $^{nat}InCl_3$, 0.25M NaOAc or EtOH, $^{111}InCl_3$, 0.25M NaOAc.

Preparation of Compound (8)

Compound (7) (280 mg) was dissolved in 10 mL Methanol and 1 mL of 47% HI was added and then mixture heated at 65° C. for 3 h. The reaction was then cooled to (0-5) ° C. in an ice bath for 1 h and the resulting precipiated collected by filtration and washed with a small volume of cold methanol. The product was then dried overnight in the vacuum oven at 40° C. to provide pure (8) (255 mg, 91%). $^1$H NMR (CDCl$_3$, 400 MHz): δ8.10 (t, 3H, J=13.0), 7.72 (d, 1H, J=7.9), 7.42 (d, 1H, J=7.3), 7.36 (t, 1H, J=7.7), 7.23 (t, 1H, J=7.6), 7.10 (d, 1H, J=8.3), 7.05 (d, 1H, J=8.0), 6.64 (t, 1H, J=12.5), 6.15 (d, 2H, J=13.5), 4.36 (s, 2H), 3.89-4.10 (m, 4H), 1.69-1.91 (m, 12H), 1.13-1.49 (m, 83H), 0.87 (t, 6H, J=6.6). Expected M$^+$ ($C_{70}H_{119}N_3$)=1000.93; Observed M$^+$=1001.0.

Preparation of Compound (9)

Compound (8) (154 mg, 0.123 mmol), DOTA-mono-NHS-tris($^t$butylester).HPF$_6$(Macrocyclics, TX) (100 mg, 0.123 mmol), diisopropylethylamine (20 μL) were stirred in dichloromethane (5 mL) at RT for 2 h. The product was then purified via silica gel chromatography eluting with dichloromethane plus an increaing amount of methanol (0 to 3%) to furnish pure (9) (70 mg, 28%). $^1$H NMR (CDCl$_3$, 400 MHz): δ8.04-7.93 (m, 2H), 7.49-7.43 (m, 1H), 7.37 (dd, 3H, J=16.1), 7.22 (t, 1H, J=7.4), 7.09-7.00 (m, 2H), 6.53 (t, 1H, J=12.5), 6.13-5.98 (m, 2H), 4.59-4.35 (m, 2H), 4.02-3.82 (m, 4H), 3.62-3.37 (m, 4H), 3.25-3.11 (m, 2H), 3.06-2.77 (m, 6H), 2.25-2.06 (m, 2H), 1.83-1.70 (m, 14H), 1.70-1.54 (m, 6H), 1.52-1.40 (m, 27H), 1.39-1.36 (m, 3H), 1.35-1.19 (m, 68H), 0.884 (t, 6H, J=6.8). Expected M+H ($C_{98}H_{169}N_7O_7$)=1556.3; Observed M+H=1556.0.

Preparation of Compound (10)

Compound (9) (70 mg, 0.042 mmol) was stirred in a mixture of TFA/dichloromethane (60:40) (10 mL) at RT overnight. The reaction mixture was then concentrated and dried under high vacuum to provide the product (40 mg, 57% yield). $^1$H NMR (DMSO-d$_6$, 400 MHz): δ8.79-8.66 (m, 1H), 8.33-8.24 (m, 2H), 7.58 (d, 1H J=7.0), 7.47 (s, 1H), 7.36 (d, 2H, J=4.2), 7.30-7.26 (m, 1H), 7.60-7.56 (m, 1H), 6.87-6.81 (m, 1H), 6.52 (t, 1H, J=12.3), 6.24 (dd, 1H, J=6.7), 4.36-4.30 (m, 1H), 4.11-3.99 (m, 3H), 3.61-3.56 (m, 3H), 3.03-2.93 (m, 10H), 1.87 (s, 1H), 1.66-1.61 (m, 12H), 1.37-1.08 (m, 79H), 0.803 (t, 6H, J=6.8). Expected M$^+$ ($C_{86}H_{144}N_7O_7$)=1387.0; Observed M$^+$=1387.0.

Preparation of Compound (11)

Compound (8) (20 mg) was dissolved in methanol (2 mL) and a solution of indium trichloride hexahydrate (9.9 mg) in 0.25M sodium acetate, pH=6 (0.67 mL) was added. The resulting reaction mixture was stirred at RT for 2 h (a small precipitation was observed almost immediately). The product was purified via normal phase silica gel chromatography eluting with an increasing amount of methanol (1 to 10%) in dichloromethane (8 mg, 37%). Expected M$^+$ ($C_{86}H_{141}N_7O_7In$)=1498.8; Observed M$^+$=1499.0.

Example 2: Preparation of Example Compounds (as Shown in Scheme 2)

The amine functionalized dye (8) was reacted with glutaric anhydride to provide (12). Standard coupling of (12) with 2-(4-aminobenzyl) diethylenetriamine penta-t-butyl acetate (www.macrocyclics.com) using HATU provided (13) which was purified via column chromatography and isolated in high yield. Removal of the t-butyl esters from (13) was accomplished by treating with TFA in dichloromethane to furnish the free acid (14). (14) was used to prepare both natural and indium-111 labeled (15) using methods similar to those described above for labeling (10).

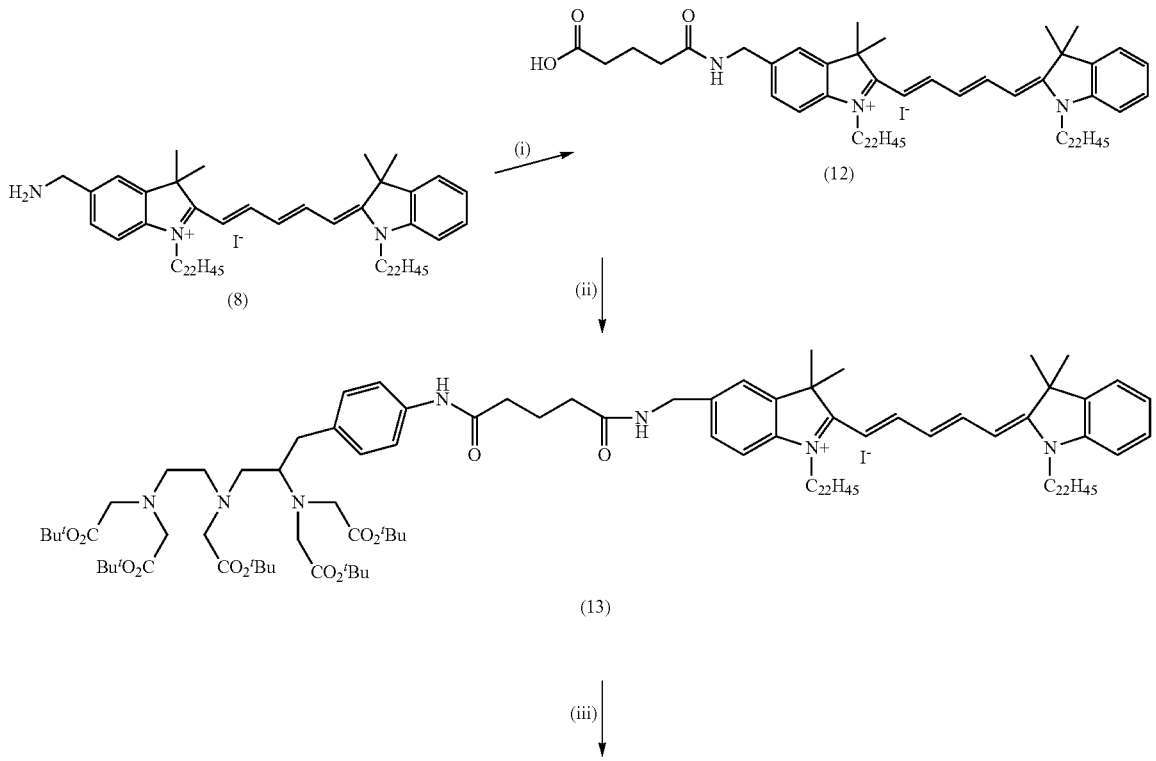

Scheme 2

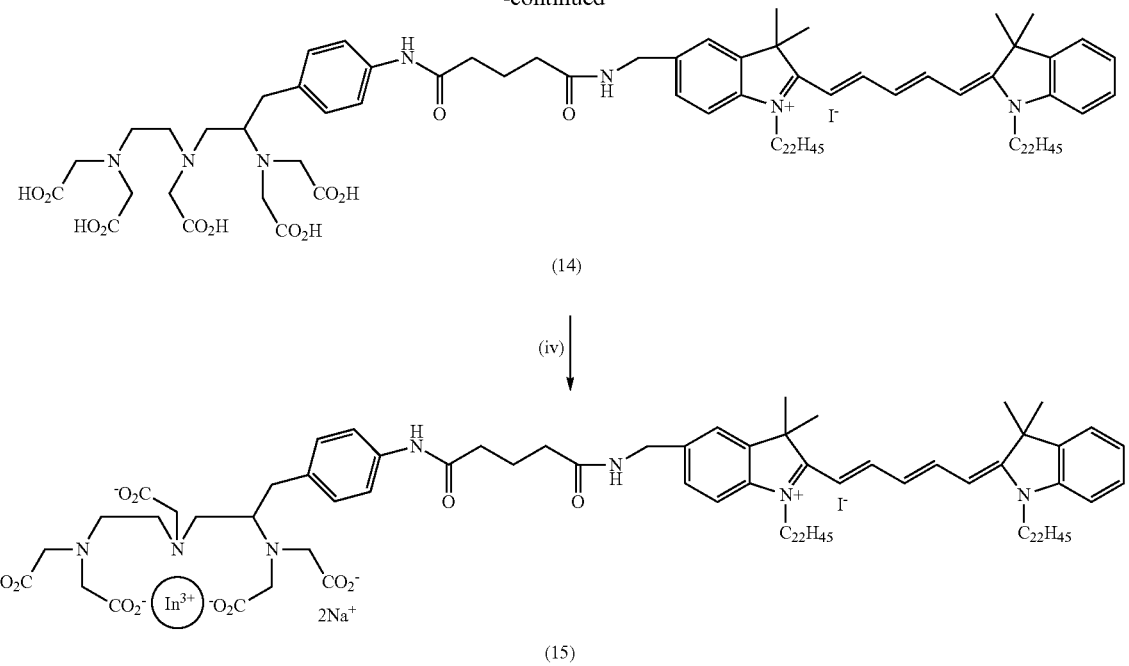

(14)

(iv)

(15)

Scheme 2 shows synthetic scheme for preparing non-radioactive and radioactive indium labeled compounds of the invention with a DTPA chelator. Reagents: (i) glutaric anhydride (ii) 2-(4-aminobenzyl) diethylenetriamine penta-t-butyl acetate, HATU (iii) TFA/CH$_2$Cl$_2$ (60:40) (iv) EtOH, $^{nat}$InCl$_3$, 0.25M NaOAc or EtOH, $^{111}$InCl$_3$, 0.25M NaOAc.

Example 3. Stem Cells Labeling with MTTI-157 (No $^{111}$In)

TC1 wild type mouse embryonic stem (mES) cells were cultured in M15 medium (high glucose DMEM with 2 mM glutamine, 100 U/ml Pen/Strep, 0.1 mM beta mercaptoethanol, 15% FBS and 1000 U/ml murine leukemia inhibitory factor) on a freshly prepared gelatinized 100-mm tissue culture dish at 37° C. in a humidified atmosphere with 5% CO$_2$. Medium was changed every day and cells passed every other day. For labeling with MTTI-157, the TC1 wild type mES cells were trypsinized, collected from the dishes, and washed twice with high glucose DMEM without serum. The washed cells were resuspended in Diluent C at the concentration of 2×10$^7$ cells/ml. Immediately, prior to staining, a 2× working stock solution of MTTI-157 (4 μM, and 20 μM) was prepared in Diluent C. Then 1 ml of the cell suspension was added rapidly into 1 ml of the 2× working dye solution and immediately mixed by pipetting. The final staining solutions were 2 μM and 10 μM. After incubation for 5 min at RT with constant mixing by pipetting up and down, the staining was stopped by adding an equal volume of 1% BSA and incubating for 1 min at RT. Subsequently, the cell suspension was centrifuged at 400 g for 10 min, and the cells were washed 3 times with 10 ml of DMEM with serum to remove unbound dye. After labeling, the cell viability was determined by trypan blue.

The MTTI-157 labeled mES cells were seeded into 12-well plates with about 0.5×10$^6$ cells per well to grow under normal culture conditions to evaluate cell viability, differentiation, fluorescence dye stability, and dye partitioning to daughter cells over time. Unlabeled normal TC1 wild type mES cells were used as control. The cell associated fluorescence was detected from the plates on an Olympus IX 70 Inverted Light Microscope (Olympus America, Inc., NY) using a Cy5 filter on Days 0, 1 and 4 after seeding.

After dye labeling, the trypan blue staining was performed to detect cell viability. The trypan blue staining analysis indicated that cell viability was more than 90% at both 2 μM and 10 μM of dye. The fluorescence microscopy analysis on Days 0, 1 and 4 are presented in FIG. 2. The fluorescence is shown in red and paired with the phase-contrast image on its right. Row 1 (top row) shows the controls with the unlabeled mES cells over the 4 days. The cells exhibit normal growth and differentiation, beginning as single cells (Day 0) and growing into larger multi-cellular masses over the four days. Row 2 (middle row) shows the mES cells labeled with MTTI-157 at 2 μM, and Row 3 (bottom row) are the cells labeled at 10 μM. It is obvious from Rows 2 and 3 that the MTTI-157 incorporated into the mES cells. On Day 0 the phase-contrast image shows cells shortly after plating in their single cellular form. By the next day (Day 1), the cells begin to merge forming clones, as expected, and the fluorescence is seen distributed within the clones with passage to other members of the cell cluster, i.e., the daughter cells. On Day 4, the cell clusters are now larger and more cells within the cluster appear to carry the fluorescence signal. Through Day 4 cell viability was preserved at both 2 μM and 10 μM dye with no obvious effects on cellular differentiation.

Cell viability and differentiation not effected by dye concentration.

Example 4. SPECT/CT and Optical Imaging of TC1 Wild Type Mouse Embryonic Stem Cells Labeled with $^{111}$In-MTTI-157 in Nude Mice: First Example All animal experiments were approved by the Institutional Animal Care and Use Committee of the university. Male NU/NU mice from Charles River Laboratories International, Inc. (Wilmington, Mass.), about 8 week-old, were used here, and fed a white chow (AIN-93G Purified Diet, Harlan, Madison, Wis.) and water, and housed under standard conditions. TC1 wild type mES cells were labeled with $^{111}$In-MTTI-157 at the dye concentration of 20 µM with about 50 µCi/ml per labeling mix according to the method described before. Then about 4-5 µCi of $^{111}$In-MTTI-157 labeled cells in 0.1 ml PBS ($5 \times 10^6$ per mouse) was injected into NU/NU mice by tail vein or delivered subcutaneously on the left shoulder. The mice were followed by SPECT/CT imaging (NanoSPECT/CT, Bioscan, Inc., Washington, D.C.) with scans at 1 h and 19 h for injection subcutaneously, and at 30 min and 18 h for injection by tail vein.

The whole body radioactivity was measured through day 9 after injection by placing the mouse in a dose calibrator (Capintec).

The SPECT image parameters were 1.0 mm/pixel, 256×256 frame size and 60 sec per projection with 24 projections. Acquisition time was approximately 30 min. During imaging, the animal was anesthetized with 1-2% isoflurane in 1.5 liters/min oxygen. A CT scan was acquired prior to the SPECT scan and was performed at standard resolution, using a 45 kVp voltage and 500 milliseconds exposure time. The CT and SPECT reconstruction was performed using InVivoScope 1.43 software (Bioscan, Washington, D.C.).

Optical images (Pearl Imager, LiCor Biosciences, Lincoln, Nebr.) were acquired on day 0 and at intervals through day 28. After imaging, the lungs, liver, spleen and teratoma were removed, imaged and then imbedded in OCT in preparation for frozen section fluorescence microscopy. Slides were counter stained with the general membrane stain D275 (Invitrogen, Em: 484 nm, Ex: 501 nm). Slides were viewed in an Olympus IX 70 Inverted Light Microscope (Olympus America, Inc., NY) using filters for FITC (for D275) and Cy5 (for MTTI-157). The frozen sections were also stained with hematoxylin-eosin (HE).

For the injection by tail vein, the SPECT/CT image (FIG. 3) showed that the radioactivity accumulated in the lungs at 1 h after injection and then distributed to liver and spleen by 19 h. For the mouse injected subcutaneously on the left shoulder, the radioactivity was retained in the shoulder and did not distribution to other tissue through 18 h (FIG. 4). The whole body radioactivity measurements corrected for decay (FIG. 5) indicated that the radioactivity was retained in the body through day 9. Collectively, these data indicate that the $^{111}$In-MTTI-157 incorporated into the stem cells and remained cell bound—the activity was not observed in organs of excretion (kidneys, bladder or intestinal tract)—and the activity remained in the body over 9 days—thus was stable in vivo. The time point in FIG. 5 at Day7 was lower than other points due to the low radioactivity and measurement accuracy.

Optical images in mice injected with $^{111}$In-MTTI-157 labeled stem cells subcutaneously on the left shoulder was performed through day 14. The stem cells in the shoulder developed into a solid teratoma over the 14 days, measuring about 250×170 mm (l×w) when removed on day 14. The optical images (FIG. 6) show a strong fluorescence signal retained on the shoulder injected with $^{111}$In-MTTI-157 labeled stem cells though day 9, while no fluorescence is observed on the opposite shoulder. The fluorescence signal appears to grow weaker by day 13 and 14 as the teratoma grew larger, but this was due to the signal now associated with cells located within the more central mass and at depth, so detection by optical imaging was more limited as expected. The optical images (FIG. 7) of the teratoma removed from the mouse and cut in half shows the strongest fluorescence signal in the teratoma center. The optical images (FIG. 7) of the excised liver, lungs and spleen from a mouse sacrificed on day 10 after injection by tail vein of $^{111}$In-MTTI-157 labeled stem cells showed fluorescence signal from the tissues. Fluorescence microscopy of these same tissues also shows fluorescence in frozen sections from liver, lungs, spleen and teratoma (FIG. 8). HE staining (FIG. 9) indicates that teratomas (red arrow showed) formed in the lungs and liver from the mouse injected by tail vein with $^{111}$In-MTTI-157 labeled stem cells and no teratoma was observed in the spleen.

Example 5. Stem Cells Labeled with MTTI-157 to Define Optimum Dye Concentration for High Dye Incorporation and Cell Labeling Efficiency: Analysis by Flow Cytometry Wild type mouse embryonic stem (mES) cells BL/6 were cultured under normal conditions, trypsinized, collected from the dishes, and washed twice with high glucose DMEM without serum. Then the washed cells were resuspended in Diluent C at the concentration of $2 \times 10^7$ cells/ml. Immediately, prior to staining, a set of 2× working MTTI-157 stock solutions at 4 µM, 20 µM, 40 µM were prepared in Diluent C. Cell suspensions of 1 ml were added rapidly to the 1 ml of 2× working dye stock and immediately mixed by pipetting (final concentrations of 2 µM, 10 µM, and 20 µM). After incubation for 5 min at RT with pipetting up and down constantly, the staining was stopped by adding an equal volume of 1% BSA and incubating for 1 min at RT. Subsequently, the cells suspension was centrifuged at 400 g for 10 min. Then the cells were washed 3 times with 10 ml of DMEM with serum to remove unbound dye. After labeling, the cell viability was determined by trypan blue. After washing, the cells were resuspended in 1% paraformaldehyde for flow cytometry analysis. Unlabeled BL/6 cells were used as a control.

Wild type mES cells BL/6 were labeled with MTTI-157 at the final concentrations of 2 µM, 10 µM, and 20 µM and analyzed by flow cytometry. Trypan blue staining indicated that the cell viability was over 90% after labeling at the dye concentrations from 2 µM to 20 µM. Flow cytometry analysis showed that the percent of labeled cells in total cells was 9.8% at 2 µM, 28.7% at 10 µM, and 34% at 20 µM (FIG. 10). The incorporation of MTTI-157 dye into stem cells is low, even at the high dye concentration of 20 µM. For further study, it is necessary to improve the dye incorporation into the stem cells.

Example 6. BL/6 Wild Type Mouse Embryonic Stem Cells (mES) Labeled with $^{111}$In-MTTI-157 in Nude Mice: SPECT/CT and Optical Imaging: Second Example The fate of BL/6 wild type mES cells labeled with $^{111}$In-MTTI-157 delivered by tail vein or subcutaneously on the shoulder was followed by SPECT/CT and optical imaging.

BL/6 wild type mouse embryonic stem cells (mES) were labeled with $^{111}$In-MTTI-157 at the concentration of 12 µM and about 250 µCi/ml according to the method described before. The labeled cells (5 in 0.1 ml PBS ($5 \times 10^6$ per mouse) were injected into NU/NU mice by tail vein or subcutaneously on the left shoulder. SPECT/CT imaging was done at 30 min, 21 h and day 4 after injection subcutaneously, and at 1 h, 22 h and day 4 when injected by tail vein. Optical imaging was performed through day 11 for the subcutaneous delivery of cells. The whole body radioactivity was measured through day 7 by placing the animal in a dose calibrator.

The lungs, liver, and spleen were removed from the mouse injected by tail vein when sacrificed on day 19, and the teratoma was removed from mouse injected subcutaneously on the left shoulder when sacrificed on day 15. Excised organs and teratoma were imaged on the Li-Cor Biosciences Pearl Imager, and then set in OCT for frozen sections. The frozen sections were stained with the general membrane fluorescent stain D275 (Invitrogen, Em: 484 nm, Ex: 501 nm) and detected on an Olympus IX 70 Inverted Light Microscope (Olympus America, Inc., NY) using a FITC filter for D275 and a Cy5 filter for MTTI-157. D275 is a cell membrane stain and was used here to stain the field of view. The frozen sections were also stained with hematoxylin-eosin (H&E) for standard microscopy.

Following the delivery by tail vein, the SPECT/CT image (FIG. 11) shows radioactivity accumulated in the lungs by 1 h following injection which then distributed to the liver and spleen by 22 h. On day 4, radioactivity in the liver and spleen is still observed. No radioactivity is seen in the kidneys, bladder, intestine or other tissues. The lack of radioactivity in these organs is an indication of the stability of $^{111}$In-MTTI-157 in vivo once incorporated into the cell membrane. For the mouse injected with cells subcutaneously on the left shoulder, the SPECT/CT images showed that the radioactivity is retained in the shoulder without distribution to other tissue and even to the muscle close to the injection site through day 4 (FIG. 12). The whole body radioactivity measurements (FIG. 5) indicate that the radioactivity is unchanged from 2 h to 21 h after injection, but then decreases slightly at 91 h and remain at this level through 165 h (7 days).

Optical images were taken of mice with $^{111}$In-MTTI-157 stem cells delivered subcutaneously on the left shoulder through day 11. These cells grew into an obvious mass termed a teratoma that retained (FIG. 13) a strong fluorescent signal though day 7. The signal was still present but weakened on day 11 due to the growth of the teratoma. The teratoma was removed after sacrifice and shown in FIG. 5 is the optical image of the mass cut in half to expose the inner area that has retained the strong fluorescent signal. The liver, lungs and spleen (FIG. 14) from the mouse sacrificed on day 19 after injection of $^{111}$In-MTTI-157 stem cells by tail vein shows different degrees of fluorescence signal in each of these tissues. The muscle was used as background for the auto fluorescence. Fluorescence microscopy (FIG. 15) of these same tissues shows obvious MTTI-157 fluorescence signal from the lungs and teratoma, the liver and spleen show limited but evidence of fluorescent areas. The lungs and liver were viewed by H&E staining (FIG. 16) and the formation of teratomas (red arrows) in these organs is evident from the mouse injected with $^{111}$In-MTTI-157 stem cells by tail vein. No evidence of a teratoma was noted in the spleen.

Example 7. MTTI-157 Labeled LS174T Cells: Test for Improved Labeling Efficiency

For improved labeling efficiency, LS174T cells labeled with MTTI-157 was tested with different conditions as shown in Table 1 and Table 2. The method for LS174T cells labeling with MTTI-157 was as described as before. Briefly, LS174T cells were trypsinized, collected, and washed twice with MEM without serum and then resuspended in Diluent C. Immediately, prior to staining; a 2× working dye stock solution in Diluent C was prepared. The cell suspension was added rapidly to an equal volume of the 2× working dye solution and immediately mixed by pipetting up. After incubation for 10 min at RT with pipetting up and down constantly, the staining was stopped by adding 1% BSA and incubating for 1 min at RT. Subsequently, the cell suspension was spun at 400 g for 5 min. The cells were washed 3 times with 10 ml of MEM with serum to remove unbound dye. After labeling, the labeled cells were fixed in 2% paraformaldehyde and analyzed by flow cytometry.

Set 1:

MTTI-157 was dissolved in ethanol at the concentration of 2 μg/μL. LS174T cells were labeled with MTTI-157 with the conditions as shown in Table 1.

TABLE 1

Labeling conditions for LS174T cells with MTTI-157 dissolved in ethanol; results of flow cytometry analysis

| | Final MTTI-157 concentration (μM) | | | | | | | | | |
|---|---|---|---|---|---|---|---|---|---|---|
| | 0 | 2 | 10 | 20 | 2 | 10 | 20 | 2 | 10 | 20 |
| Final cells concentration (×10$^7$/ml) | 1 | 1 | 1 | 1 | 10 | 10 | 10 | 1 | 1 | 1 |
| DMSO in 2x working dye stock (%) | 0 | 0 | 0 | 0 | 0 | 0 | 0 | 2 | 2 | 2 |
| % labeled cells in total cells by FACS | 4.8 | 12.6 | 62.7 | 74.3 | 29.5 | 57.9 | 75.0 | 23.7 | 55.9 | 71.1 |

Set 2:

MTTI-157 was dissolved in DMSO at the concentration of 2 μg/μL. LS174T cells were labeled with MTTI-157 at the condition as shown in Table 2.

TABLE 2

Labeling conditions for LS174T cells with MTTI-157 dissolved in DMSO; results of flow cytometry analysis

| | Final dye concentration (μM) | | | | | | |
|---|---|---|---|---|---|---|---|
| | 0 | 10 | 20 | 20 | 40 | 40 | 80 |
| Final cell concentration (×10$^7$/ml) | 10 | 10 | 10 | 20 | 10 | 20 | 10 |
| DMSO in 2x working dye stock (%) | 0 | 2 | 4 | 4 | 8 | 8 | 16 |
| % labeled cells in total cells by FACS | 0.0 | 97.3 | 97.9 | 98.6 | 99.2 | 98.5 | 99.5 |

For improved cell labeling with MTTI-157 the following were tested: two solvents (ethanol and DMSO) to dissolve MTTI-157; different cell concentrations; and different dye labeling concentrations.

In Set 1, MTTI-157 was dissolved in ethanol. The flow cytometry analysis (Table 1) showed that the dye concentration had an apparent effect on the labeling efficiency, while no obvious effect on cell labeling efficiency with increase in cell concentration or the presence of DMSO in the labeling mixture. The labeling efficiency improved as the dye concentration increased. Even at the highest final dye concentration of 20 µM, the labeling efficiency was about 70%. At the dye concentration of 2 µM, the cell labeling efficiency was higher only if the cell concentration was high, $10 \times 10^7$/ml, or if DMSO was present in the labeling mixture. But in either case the labeling efficiency did not approach 70%. At the dye concentration of 10 µM and 20 µM, no obvious difference was shown between cell concentration or the presence of DMSO in the labeling mixture.

In Set 2, MTTI-157 was dissolved in DMSO. The flow cytometry analysis (Table 2) showed that even at the final dye concentration of 10 µM, the labeling efficiency was 97.3%, which in Set 1 was only about 60% when MTTI-157 was dissolved in ethanol. This study indicates that DMSO may be better than ethanol as solvent for incorporating MTTI-157 into the cell membrane.

Example 8. Fluorescent and $^{111}$In Labeled Agent for Optical and SPECT Cell Tracking LS-174T cells were labeled with $^{111}$In-MTTI-157. Fluorescence microscopy was used to evaluate incorporation and retention in cells thru 8 days. SPECT and optical imaging was used to track distribution and retention in mice of $^{111}$In-MTTI-157-labeled LS-174T cells (about 10 µCi) delivered by tail vein.

$^{111}$In-MTTI-157 was incorporated into LS-174T cancer cells as a model for stem cells. A small volume stock solution (about 100 µL) of MTTI-157 1-2 µg/µL in 100% ethanol was made fresh each time, with storage for no longer than a week. The MTTI-157 stock solution was stored in a screw capped Eppendorf tube in the dark at RT. The labeling reaction was with 2-15 µL (61-414 µg) of MTTI-157 stock solution in a screw capped Eppendorf tube. The water content of the final radiolabeling reaction was at or less than 10%. Too high a water content and a precipitate can form. For the labeling reaction to a volume of $^{111}$InCl$_3$ (about 1 µL) was added an equal volume of 0.25 M ammonium acetate buffer pH 5.2. The sample was left for 10-15 min before transfer to the dye solution. The $^{111}$In acetate volume transferred was about 1 depending on activity required and the aqueous volume needs to be considered to avoid the precipitate. The transfer was quick with repeated mixing with the pipette. If the volume is ample, a quick spin on the vortex is done for thorough mixing. The labeling reaction mixture was placed in a water bath pre-set to 40° C. After about 5 min the water bath was turned off, and the sample left for 1-2 hrs. If there is significant evaporation-refluxing-after the incubation, the tube is spun to bring down all liquid before analyzing.

Labeling efficiency was determined by C8 HPLC (Phenomenex, Luna 5 u, C8 (2), 100 A, 250×4.6 mm, 5 micron) flow rate of 1 mL/min with a mobile phase A (90% methanol, 0.1% TFA) and mobile phase B (100% methanol, 0.1% TFA). Initial conditions were 95% A for 1 minute then gradient to 10% A at 15 minutes, and 5% at 20 min, then back to 95% at 30 min. ITLC was with silica strips (Gelman) with solvent of methanol, and 1% TFA.

The $^{111}$In-MTTI-157 incorporated into cells was followed in culture to determine the fate of both labels (fluorescence and $^{111}$In), ability to pass on to subsequent generations, and cell's retention of viability/proliferation by following cells in culture. The $^{111}$In-MTTI-157 was incorporated into LS-174T cells according to the methods described before for the CellVue family of dyes. Briefly, LS174T cells at 90% confluency were trypsinized, and washed twice with MEM without serum. The cells were resuspended in Diluent C with $2 \times 10^7$ cells/ml. Immediately, prior to staining, a 2-fold concentrated working dye stock solution was prepared in Diluent C at dye concentrations of 4 µM, 20 µM and 40 µM and with 1.7-5.2 $^{111}$In for in vitro studies and about 500 µCi for in vivo studies. To 100 µL of a cell suspension was added rapidly 100 µL of a 2× working dye solution with immediate mixing by pipette that was continued for 10 min at RT. The dye incorporation was terminated by adding an equal volume (200 µL) of 1% BSA and leaving for 1 min at room temperature (RT) before the cells were spun down (400×g for 10 min) and washed 3 times with 10 ml of MEM with serum to remove any unincorporated dye. After washing, cell viability was determined by trypan blue.

The $^{111}$In-MTTI-157 labeled LS-174Tcells were seeded into 12-well plates with about $10^6$ cells per well to grow under normal culture conditions to evaluate cell viability, dye stability, and dye partitioning to daughter cells over time. The cell-associated fluorescence was detected from the plates on an Olympus IX 70. Inverted Light Microscope (Olympus America, Inc., NY) using a Cy5 filter on days 0, 3 and 8 after seeding. On each day, samples of cells were collected, counted for cell number with a hemocytometer and radioactivity per $10^6$ cells determined by gamma well counter Na (TI) (Cobra II Auto-Gamma, Packard Instrument Co, Downer Grove, Ill.).

$^{111}$In-MTTI-157 labeled LS174T cells were administered to mice to follow their fate and that of the labels they carried. All animal experiments were approved by the Institutional Animal Care and Use Committee of the university. Male SKH-1 mice about 8 week-old (Charles River Laboratories, Inc., Wilmington, Mass.) were housed under standard conditions and fed white chow (AIN-93G Purified Diet, Harlan, Madison, Wis.). LS174T cells were prepared labeled with $^{111}$In-MTTI-157 as above, and about $5 \times 10^6$ cells with 10-12 µCi was injected by tail vein per mouse.

The mice were followed by SPECT/CT imaging (NanoSPECT/CT, Bioscan, Inc., Washington, D.C.) with scans at 30 min, 1 h, 24 h, 72 h, 120 h and 168 h following injection. The SPECT image parameters were 1.0 mm/pixel, 256×256 frame size and 60 sec per projection with 24 projections. Acquisition time was approximately 30 min. During imaging, the animal was anesthetized with 1-2% isoflurane in 1.5 L/min oxygen. A CT scan was acquired prior to the SPECT scan and was performed at standard resolution, using a 45 kVp voltage and 500 milliseconds exposure time. The CT and SPECT reconstruction was performed using InVivoScope 1.43 software (Bioscan, Washington, D.C.).

Optical images (Pearl Imager, LiCor Biosciences, Lincoln, Nebr.) were acquired on day 0 and at intervals through day 28. To facilitate detection of signal at depth, such as in the lungs, some animals were killed, the chest and abdomen opened to expose internal organs, and then imaged. Untreated mice served as control. After imaging, the lungs, liver and spleen were removed, imaged and then imbedded in OCT in preparation for frozen section fluorescence microscopy. Slides were counter stained with the general membrane stain D275 (Invitrogen). Slides were viewed in an Olympus IX 70 Inverted Light Microscope (Olympus America, Inc., NY) using filters for FITC (for D275) and Cy5 (for MTTI-157).

The MTTI-157 at 2 μg/μL ethanol was labeled with $^{111}$In in 0.25 M ammonium acetate, pH 5.2. After 1 h greater than 90% radiochemical purity was attained as shown by C18 HPLC in FIG. 17. The labeled product elutes with retention time of 18.7 min. Specific activity of 10 μCi/μg was reproducibly attained, and a maximum specific activity of 74 μCi/μg was achieved showing 89% radiochemical purity.

To determine the fate of both $^{111}$In and fluorescence labels in vitro, cells were labeled with $^{111}$In-MTTI-157 using final sample concentrations of 2 μM, 10 μM and 20 μM and grown under normal culture conditions for 8 days. The stability of both labels was determined by fluorescence microscopy and nuclear counting. After labeled dye incorporation trypan blue staining showed greater than 95% cell viability (data not shown). When a 40 μM sample concentration was used cell viability dropped to about 90% (data not shown). Bright light and corresponding fluorescence microscopy of cells labeled with 20 $^{111}$In-MTTI-157 are shown in FIG. 18 from days 0, 3 and 8. Cells show normal growth over the 8 days and demonstrate that with proliferation succeeding generations retained the fluorescence marker with no apparent effect on cell viability. With the increase in labeled dye concentration, fluorescence intensity increased.

The cell-associated radioactivity with 2, 10 and 20 μM $^{111}$In-MTTI-157 on days 0, 3, and 8 is shown in FIG. 19a. The loss of radioactivity from day 0 to day 3 is likely due to the loss of cells from initial platting, once the cells were established as indicated on days 3-8, the cell associated radioactivity did not change at each dye concentration. However, the cell number showed an increase at each dye concentration from day 3 to day 8 and the trend in cell number (growth) was comparable to the control cells with no dye (FIG. 19b).

$^{111}$In-MTTI-157 labeled LS174T cells were injected into SKH-1 mice by tail vein to evaluate the fate of both labels in vivo. Mice were followed by SPECT/CT over the course of 7 days and by optical imaging over 28 days. SPECT/CT are shown in FIGS. 20a and 20b, in the earliest scan at 30 min and 1 h radioactivity is restricted to the lungs and then seen to redistribute within a day to the liver and spleen with some remaining in the lungs in the case of image FIG. 20b.

SPECT scans through day 7 show the distribution unchanged with only lungs, liver and spleen apparent out to day 5-7. No radioactivity in kidneys and bladder was obvious on any day. The lack of activity in gut, kidneys and bladder indicates the stability of the labeled dye on the cells.

Whole body radioactivity measurements by dose calibrator is shown in (FIG. 21) as the percent of injected activity remaining (half-life corrected) starting at 5 min (on day 0) through day 14. The loss of activity from day 0 to day 10 (across four half-lives) was about 23%. Beyond 10 days radioactivity was too near background for accurate determination. These data show that $^{111}$In-MTTI-157 labeled cells were stable in vivo, and the labeled dye $^{111}$In-MTTI-157 itself is stable.

Whole body optical images acquired of the same mice but followed through day 28 are shown in FIG. 22. As with SPECT the early optical images show fluorescence signal in the lungs on day 0 that is still apparent on day 28 (in comparison to signal in control animal lungs). As with the SPECT scans by the first day the signal distributes to the liver and spleen, and is still obvious in the optical scans through day 28. Confirmation was obtained from excised organs. Shown are excised lungs, liver and spleen from an untreated mouse (top row) and treated mice optical scans from days 1, 7, 14 and 28 of excised lungs, liver and spleen (FIG. 23).

Further examination of lungs, liver and spleen by fluorescence microscopy confirm the retention of the MTTI-157 in these tissues through day 28 as shown in FIG. 24. The sections were treated with the membrane lipophilic dye D275 (green) to define the field of view and the MTTI-157 signal (red) is apparent in lungs through day 14 and in liver through day 28. These data are consistent with the results from SPECT/CT and optical imaging.

SPECT/CT scans of mice receiving $^{111}$In-MTTI-157 labeled cells by tail vein showed radioactivity restricted to the lungs in the earliest scans on Day 0, but redistributed by the next day to include the liver and spleen. Through Day 7 distribution was unchanged with only lungs, liver and spleen apparent. No indication of $^{111}$In instability was observed as evident by the absence of activity in gut, kidneys and bladder on any day. Parallel whole body activity measurements (decay corrected) confirmed $^{111}$In retention out thru Day 14; beyond that time activity was too near background for accurate determination.

Corresponding whole body optical images showed fluorescence in the lungs and liver out through Day 28 that was confirmed by optical scans of the excised organs, including spleen. Fluorescence microscopy of tissue frozen sections confirmed cell associated MTTI-157 signal in lung thru Day 21 and liver and spleen thru Day 28.

This dual labeled cell marker, $^{111}$In-MTTI-157, has provided a means to monitor the in vivo fate of cells out through 28 days in vivo with no evidence of label instability. This cell marker will be evaluated further for tracking the fate of stem cells in vivo for potential use in cell-based therapies.

Example 9. Dyes Transfer Flow Cytometry Analysis

The human colon cancer cell line LS174T was used here as a model to identify the optimal dyes marker with minimal transfer to neighbor cells for cell tracking. A family of DiD dyes (Ex: 648 nm, Em: 667 nm) with variable lipophilic aliphatic tails (Cm/Cn here refer to lengths lipophilic aliphatic tails in the number of C atoms) were investigated: MT279 (C22/C3), MT280 (C22/C12), MT284 (C14/C3), MT285 (C14/C14), CN1012 (C20/C20), MTTI-157 without the DOTA (C22/C22). LS174T cells were cultured in minimal essential medium (MEM) with nonessential amino acids, 10% fetal bovine serum (FBS) and 1% penicillin/streptomycin at 37° C. in a humidified atmosphere with 5% $CO_2$ and were passaged weekly.

Optimization of Dye Concentrations

Cell labeling efficiency was observed as being different with the six dyes, so did this study to select a concentration that would give at least 100% of cells labeled with a fluorescence intensity that was similar among the group of six dyes. Not all dyes labeled cells at a similar level. Some dyes (like MT284) gave results that were noted as being too bright for reliable FACS analysis. Thus different dye concentrations were investigated looking for the ideal concentration for each dye.

Four working dye stock solutions were investigated. LS174T cells were trypsinized, collected, and washed twice with MEM without serum when the flask was 90% confluent. The washed cells were resuspended in Diluent C at the concentration of $2 \times 10^7$ cells/ml. Immediately, prior to staining, 2× working dye stock solutions (1 μM, 4 μM, 10 μM or 20 μM) in Diluent C were prepared. Then 500 μl of cell suspension was added rapidly into 500 μl of 2× working dye and immediately mixed by pipetting. After incubation for 10 min at room temperature with pipetting up and down constantly, the staining was stopped by adding equal volume (1000 μL) of 1% BSA and incubating for 1 min at room temperature. Subsequently, the cells suspension was centrifuged at 400 g for 10 min. Then the cells were washed 3 times with 10 ml of MEM with serum to remove unbound dye. After labeling, the cell viability was determined by trypan blue. The labeled cells were fixed in 2% paraformaldehyde and analyzed by flow cytometry.

The cells were labeled at 0.5 μM, 2 μM, 5 μM or 10 μM and analyzed by flow cytometry to determine the optimum concentration. The flow cytometry analysis (FIG. 25) showed that the fluorescence intensity per cell increased as the dye concentration increased. At the same concentration, the fluorescence intensity per cell for the dyes indicated that MT284 (C14/C3)>MT279 (C22/C3)>MT280 (C22/C12)>MT285 (C14/C14)>CN1012 (C20/C20)>MTTI-157 (C22/C22). Especially for MT284, the fluorescence intensity was over the detection range of flow cytometry even at low labeling concentration (0.5 μM). The results suggest that it is easier for dyes with shorter carbon tails to incorporate into the cell membrane. For dyes MT279, MT280, MT284 and MT285, 100% of the cells were labeled even at the lowest dye concentration of 0.5 μM, and of course remained at 100% as dye concentration increased. While for dye CN1012, the percent of cells labeled at the concentrations of 0.5 μM, 2 μM, 5 μM or 10 μM was 93.1%, 99.5%, 99.9%, 100% respectively, and for MTTI-157 it was 71.5%, 92.3%, 98.6%, 99.4%, respectively (FIG. 26).

Evaluation of Dye Transfer: Co-Culture of Dye Labeled and Unlabeled Cells

LS174T cells were trypsinized, collected, and washed twice with MEM without serum and labeled with the six dyes according to the method described above. Briefly, the washed cells were resuspended in Diluent C at the concentration of $2 \times 10^7$ cells/ml. immediately, prior to staining, 2× working dye stock in Diluent C were prepared. Study sets are described below. One (1) ml of the cell suspension was added rapidly to 1 ml of 2× working dye solution and immediately mixed by pipetting. After incubation for 10 min at room temperature with pipetting up and down constantly, the staining was stopped by adding an equal volume (2 ml) of 1% BSA and incubating for 1 min at room temperature. Subsequently, the cells suspension was spun at 400 g for 10 min. Then the cells were washed 3 times with 10 ml of MEM with serum to remove unbound dye. The cell viability was determined by trypan blue staining. The dye labeled cells were co-cultured with an equal number of unlabeled cells under normal culture conditions. Samples were removed at 0 h, 24 h and 48 h after initiation of co-culture and fixed in 2% paraformaldehyde for flow cytometry analysis.

Set 1:

Six dyes: MT279, MT280, MT284, MT285, CN1012, MTTI-157, were used for cell labeling at the final concentration in the labeling mix of 2 μM for each dye.

LS174T cells were labeled with the 6 dyes at 2 μM and co-cultured with an equal number of unlabeled cells. FIG. 27 shows the percent of labeled cells at different time points after co-culture from flow cytometry analysis. The percent of unlabeled cells incorporating dye from labeled cells for each dye at 24 h, 48 h after co-culture compared to that at 0 h is shown in Table 3. From the data in Table 3 it appears that MT284 is the best dye, showing no transfer to unlabeled cells. But, in FIG. 27, dye MT284 showed at 0 h of co-culture, already about 100% of the cells were labeled. It is possible that the dye transfer occurred when the samples were fixed and stored at 4° C. and held for 48 h prior to flow cytometry analysis. So these data may not accurately represent the true situation. Therefore to avoid this possibility, in the next study for the 0 h sample, the labeled cells and unlabeled cells were collected and fixed separately, and then mixed immediately before flow cytometry analysis.

TABLE 3

Percent of unlabeled cells incorporating dye from labeled cells for each dye at 24 h and 48 h of co-culture compared to the value at 0 h.

|  | MT279 | MT280 | MT284 | MT285 | CN1012 | MTTI-157 |
|---|---|---|---|---|---|---|
| 24 h | 16.68 | 9.03 | −0.74 | 4.23 | 20.69 | 22.39 |
| 48 h | 18.36 | 13.83 | −2.06 | 6.8 | 22.6 | 22.74 |

Set 2:

Six dyes: MT279, MT280, MT284, MT285, CN1012, MTTI-157 were used for the cell labeling at the optimum concentration determined. The final concentration in the labeling reaction for the dyes were respectively: 0.5 μM, 2 μM, 0.25 μM, 2 μM, 5 μM and 10 μM. Based on the results of optimization of dye concentration study, at these concentrations the cells were 100% labeled (all cells carried a label) and had a similar mean fluorescence intensity when analyzed by FACS.

Based on the results of the optimization of dye concentration study, the labeling concentrations for the dyes were selected as follows: 0.5 μM, 2 μM, 0.25 μM, 2 μM, 5 μM and 10 μM for dyes MT279, MT280, MT284, MT285, CN1012, and MTTI-157 respectively. These concentrations were used to ensure that 100% of the cells were labeled and carried a similar mean fluorescence intensity. Also, for the sample at 0 h, the labeled cells and unlabeled cells were collected and fixed separately, and mixed immediately before flow cytometry analysis. The flow cytometry results are shown in FIG. 28. The percent of unlabeled cells incorporating dye from labeled cells for each dye at 24 h and 48 h of co-culture compared to that at 0 h is shown in Table 4. The results collectively show that at low dye concentrations, i.e., 0.5 μM, 2 μM, and 2 μM for MT279, MT280, and MT285, no dye transfer to unlabeled cells occurred. Dye MT284 appears to be the most efficient dye to transfer. Dye MTTI-157 showed transfer as well but with 22% at 24 h and 28% at 48 h. Dye CN1012 showed lower transfer than MTTI-157, with 8% at 24 h and 15% at 48 h.

TABLE 4

Percent of unlabeled cells incorporating dye from labeled cells for each dye at 24 h and 48 h after co-culture compared to the value at 0 h.

|  | MT279 | MT280 | MT284 | MT285 | CN1012 | MTTI-157 |
|---|---|---|---|---|---|---|
| 24 h | −6.13 | −3.59 | 60.33 | −5.3 | 8.115 | 22.17 |
| 48 h | −2.9 | −0.1 | 58.64 | 4.92 | 14.93 | 28.45 |

Set 3:

Since in Set 2, some dyes (MT279, MT280 and MT285) showed no transfer at the concentrations selected for testing, Set 3 was done at another set of concentrations to verify whether dye will transfer if a higher concentration was used, and it did. Six dyes: MT279, MT280, MT284, MT285, CN1012, and MTTI-157 were used for the cells labeling.

The final concentrations in the labeling reaction for the dyes were 5 μM except for MT284, which was tested again at 0.25 μM.

LS174T cells were labeled with the six dyes MT279, MT280, MT284, MT285, CN1012, and MTTI-157, respectively. The final dye concentration in the labeling reaction in this case was 5 μM except for MT284, which was tested again at 0.25 μM.

The labeled cells were co-cultured with unlabeled cells, and as before at 0 h, the labeled cells and unlabeled cells were collected and fixed separately, and mixed immediately before flow cytometry analysis. The flow cytometry results are shown in FIG. 29. The percent of unlabeled cells incorporating dye from labeled cells for each dye at 24 h and 48 h of co-culture compared to that at 0 h is indicated in Table 5. This study showed that at this higher dye concentration (5 μM), all six dyes transferred from labeled cells to unlabeled cells. As indicated in Table 5, MT285 showed the least transfer, and again PITR284 showed the highest transfer even at the lower concentration (0.25) (about all the unlabeled cells took in dye from labeled cells).

TABLE 5

Percent of unlabeled cells incorporating dye from labeled cells for each dye at 24 h and 48 h of co-culture compared to the value at 0 h.

|  | MT279 | MT280 | MT284 | MT285 | CN1012 | MTTI-157 |
| --- | --- | --- | --- | --- | --- | --- |
| 24 h | 25.88 | 10.76 | 48.23 | −2.36 | 12.9 | 6.93 |
| 48 h | 39.42 | 26.85 | 48.36 | 17.27 | 24.46 | 22.16 |

Set 4:

Based on Set 2 and Set 3 results, Set 4 was done. Here only these three dyes: MT280, MT285, and MTTI-157 were used for the cells labeling. These three dyes were the best and each was tested at 3 concentrations to determine the best concentration for labeling. The dye final concentrations for labeling were 0.5 μM, 2 μM, and 5 μM.

LS174T cells were labeled with the six dyes separately and co-cultured with unlabeled cells to identify the optimal dye marker showing minimal transfer to neighboring cells. Samples were collected at 0 h, 24 h and 48 h of co-culture and fixed in 2% paraformaldehyde for flow cytometry analysis.

From the previous studies, MT280 and MT285 showed the least amount of dye transfer and were selected for further evaluation along with MTTI-157. In this study, the three dyes were each labeled at the following three concentrations: 0.5 μM, 2 μM, and 5 μM. (BUT these three concentrations are only ideal for MT280 and MT285, and not ideal for MTTI-157, which does not label cells as well at these low concentrations). As before, the labeled cells were co-cultured with unlabeled cells and samples were collected at 0 h, 24 h, and 48 h of co-culture and analyzed by flow cytometry. For the sample at 0 h, the labeled cells and unlabeled cells were collected and fixed separately, and mixed immediately before flow cytometry analysis. The flow cytometry results are shown in FIG. 30 as the percent of cells labeled. As is obvious in FIG. 30 for MTTI-157 the percent of labeled cells is low at these dye concentrations, especially at 0.5 μM. The more ideal labeling concentration for MTTI-157 is 10-20 μM. The percent of unlabeled cells incorporating dye from labeled cells for each dye at 24 h and 48 h of co-culture compared to that at 0 h is shown in Table 6. These data show that for MT280 and MT285, almost no transfer occurred at the low concentration of 0.5 μM. For MTTI-157, at the concentration of 0.5 dye transfer took place. At the concentrations of 2 μM and 5 all the three dyes transferred from labeled cells to unlabeled cells. At these two dye concentrations transfer to unlabeled cells with each of the three dyes was similar as is apparent from the values in Table 6.

TABLE 6

Percent of unlabeled cells incorporating dye from labeled cells for each dye at 24 h and 48 h of co-culture compared to that at 0 h.

|  | 24 h | 48 h |
| --- | --- | --- |
| MT280 (0.5 μM) | 1.675 | 1.29 |
| MT280 (2 μM) | 25.095 | 28.19 |
| MT280 (5 μM) | 40.84 | 40.905 |
| MT285 (0.5 μM) | 5.07 | 7.835 |
| MT285 (2 μM) | 24.99 | 28.285 |
| MT285 (5 μM) | 35.155 | 34.195 |
| MTTI-157 (0.5 μM) | 13.58 | 14.675 |
| MTTI-157 (2 μM) | 23.555 | 25.615 |

In this specification and the appended claims, the singular forms "a," "an," and "the" include plural reference, unless the context clearly dictates otherwise.

Unless defined otherwise, all technical and scientific terms used herein have the same meaning as commonly understood by one of ordinary skill in the art. Although any methods and materials similar or equivalent to those described herein can also be used in the practice or testing of the present disclosure, the preferred methods and materials are now described. Methods recited herein may be carried out in any order that is logically possible, in addition to a particular order disclosed.

INCORPORATION BY REFERENCE

References and citations to other documents, such as patents, patent applications, patent publications, journals, books, papers, web contents, have been made in this disclosure. All such documents are hereby incorporated herein by reference in their entirety for all purposes. Any material, or portion thereof, that is said to be incorporated by reference herein, but which conflicts with existing definitions, statements, or other disclosure material explicitly set forth herein is only incorporated to the extent that no conflict arises between that incorporated material and the present disclosure material. In the event of a conflict, the conflict is to be resolved in favor of the present disclosure as the preferred disclosure.

EQUIVALENTS

The representative examples are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples and the references to the scientific and patent literature included herein. The examples contain important additional information, exemplification and guidance that can be adapted to the practice of this invention in its various embodiments and equivalents thereof.

What is claimed is:

1. A method for performing cell therapy, comprising:
   administering to a subject cells labeled with a compound having the formula:

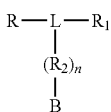

wherein
B is a chelating moiety capable of complexing to a radioactive metal;
R and $R_1$ are substituent groups independently selected from the group consisting of alkyl, alkenyl, alkynyl, alkaryl and aralkyl, each of R and $R_1$ comprising one or more linear or branched hydrocarbon chains having from about 2 to about 30 carbon atoms, and each of R and $R_1$ being unsubstituted or substituted with one or more non-polar functional groups;
L comprises a fluorophore with emission in the range from about 650 nm to about 850 nm;
$R_2$ is a spacer moiety having the formula:

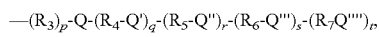

wherein
$R_3$ is an aliphatic hydrocarbon, $R_4$, $R_5$, $R_6$ and $R_7$ are independently selected from the group consisting of aliphatic, alicyclic or aromatic hydrocarbons, heterocycles or $CH_2C(CO_2H)=CH$,
Q, Q', Q", Q''' and Q'''' are linking groups independently selected from the group consisting of amide, thiourea, hydrazone, acylhydrazone, ketal, acetal, orthoester, ester, anhydride, disulfide, urea, carbamate, imine, amine, ether, carbonate, thioether, sulfonamide, carbonyl, amidine and triazine, a valence bond, the aliphatic or alicyclic hydrocarbons having from about 1 to about 12 linear carbon atoms, and the aromatic hydrocarbons having from about 6 to about 12 carbon atoms;
p, q, r, s and t each is 0 or 1; and
n is 0 or 1; and
tracking the cells via two or more modalities comprising optical imaging and radiological imaging of the labeled cells.

2. The method of claim 1, wherein the cells are stem cells.
3. The method of claim 1, wherein B is complexed to $^{111}$In ion.
4. The method of claim 1, wherein the compound has the formula:

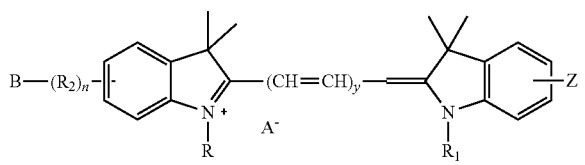

wherein
Z is a substituent selected from the group consisting of H, alkyl, OH, O-alkyl, COOH, $CONH_2$, $SO_3H$, $SO_2NH_2$, CONH-alkyl, $CON(alkyl)_2$, NH-acyl, NH-alkyl, $N(alkyl)_2$, SH, S-alkyl, $NO_2$, halogen, $Si(alkyl)_3$ and $O-Si(alkyl)_3$, wherein the alkyl groups independently comprising from 1 to 4 carbon atoms;
y is 2 or 3; and
A is a biologically compatible counter anion.

5. The method of claim 4, wherein B is complexed to $^{111}$In ion.

6. The method of claim 1, wherein the compound has the formula:

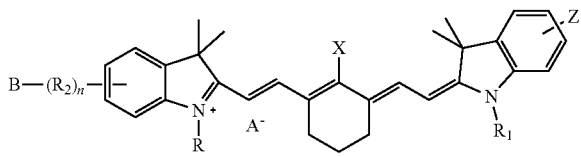

wherein
Z is a substituent selected from the group consisting of H, alkyl, OH, O-alkyl, COOH, $CONH_2$, $SO_3H$, $SO_2NH_2$, CONH-alkyl, $CON(alkyl)_2$, NH-acyl, NH-alkyl, $N(alkyl)_2$, SH, S-alkyl, $NO_2$, halogen, $Si(alkyl)_3$ and $O-Si(alkyl)_3$, wherein the alkyl groups independently comprising from about 1 to about 4 carbon atoms;
X is a substituent selected from the group consisting of H, halogen, phenoxy, thiophenoxy and aryl; and
A is a biologically compatible counter anion.

7. The method of claim 6, wherein B is complexed to $^{111}$In ion.

8. The method of claim 1, wherein the compound has the formula:

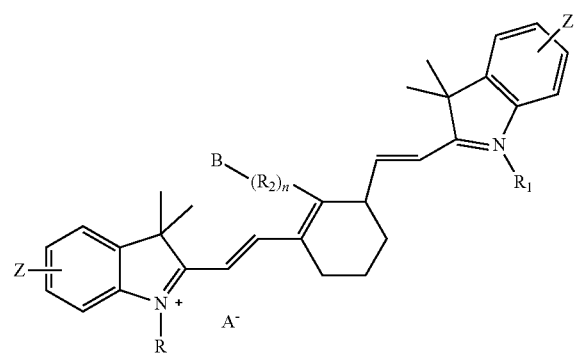

wherein
Z is a substituent selected from the group consisting of H, alkyl, OH, O-alkyl, COOH, $CONH_2$, $SO_3H$, $SO_2NH_2$, CONH-alkyl, $CON(alkyl)_2$, NH-acyl, NH-alkyl, $N(alkyl)_2$, SH, S-alkyl, $NO_2$, halogen, $Si(alkyl)_3$ and $O-Si(alkyl)_3$, wherein the alkyl groups independently comprising from about 1 to about 4 carbon atoms.

9. The method of claim 8, wherein B is complexed to $^{111}$In ion.

10. The method of claim 1, having the formula:

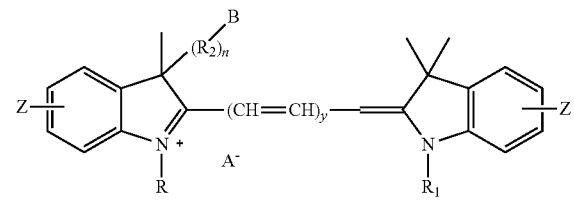

wherein
Z is a substituent selected from the group consisting of H, alkyl, OH, O-alkyl, COOH, CONH$_2$, SO$_3$H, SO$_2$NH$_2$, CONH-alkyl, CON(alkyl)$_2$, NH-acyl, NH-alkyl, N(alkyl)$_2$, SH, S-alkyl, NO$_2$, halogen, Si(alkyl)$_3$ and O—Si(alkyl)$_3$, wherein the alkyl groups independently comprising from about 1 to about 4 carbon atoms.

11. The method of claim 10, wherein B is complexed to $^{111}$In ion.

12. The method of claim 1, having the formula:

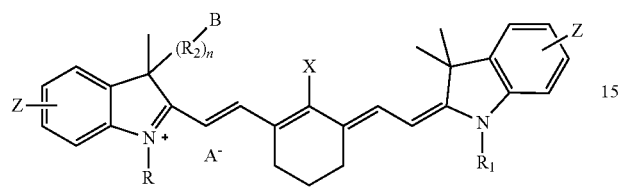

wherein
Z is a substituent selected from the group consisting of H, alkyl, OH, O-alkyl, COOH, CONH$_2$, SO$_3$H, SO$_2$NH$_2$, CONH-alkyl, CON(alkyl)$_2$, NH-acyl, NH-alkyl, N(alkyl)$_2$, SH, S-alkyl, NO$_2$, halogen, Si(alkyl)$_3$ and O—Si(alkyl)$_3$, wherein the alkyl groups independently comprising from about 1 to about 4 carbon atoms; and
X is a substituent selected from the group consisting of H, halogen, phenoxy, thiophenoxy and aryl.

13. The method of claim 12, wherein B is complexed to $^{111}$In ion.

14. The method of claim 1, wherein the compound has the formula

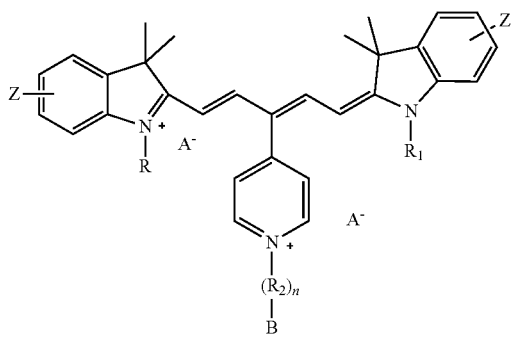

wherein
Z is a substituent selected from the group consisting of H, alkyl, OH, O-alkyl, COOH, CONH$_2$, SO$_3$H, SO$_2$NH$_2$, CONH-alkyl, CON(alkyl)$_2$, NH-acyl, NH-alkyl, N(alkyl)$_2$, SH, S-alkyl, NO$_2$, halogen, Si(alkyl)$_3$ and O—Si(alkyl)$_3$, wherein the alkyl groups independently comprising from about 1 to about 4 carbon atoms.

15. The method of claim 14, wherein B is complexed to $^{111}$In ion.

16. The method of claim 1, wherein the compound is chelated to an $^{111}$In ion, with the formed complex having the formula:

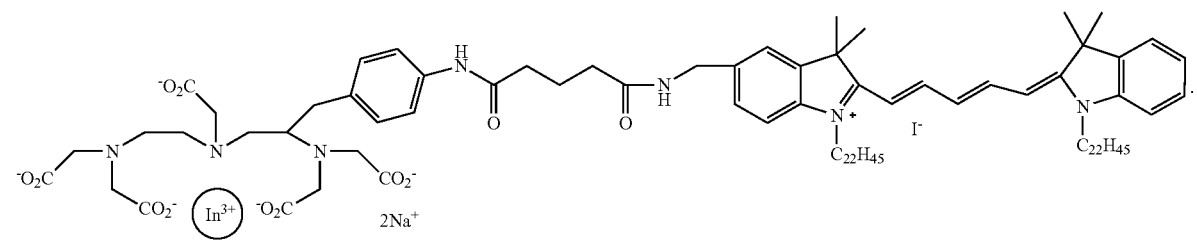

17. The method of claim 1, wherein the compound is chelated to an $^{111}$In ion, with the formed complex having the formula:

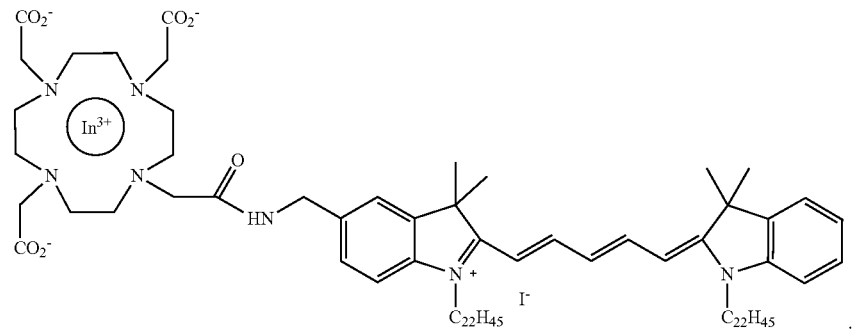

18. The method of claim 1, wherein the compound is chelated to an $^{111}$In ion, with the formed complex having the formula:
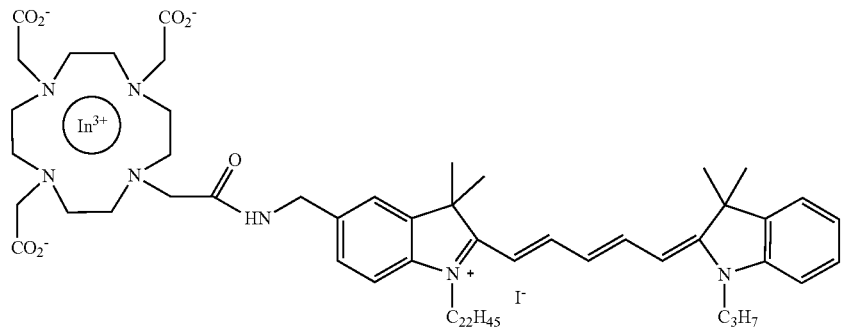
19. The method of claim 1, wherein the compound is chelated to an $^{111}$In ion, with the formed complex having the formula:
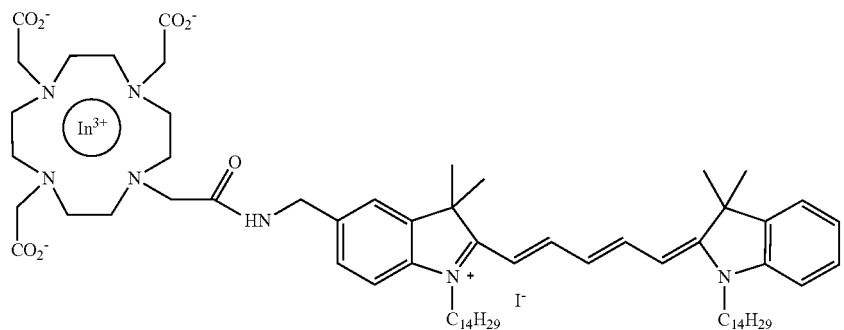
* * * * *